US008080706B2

(12) United States Patent
Stahl

(10) Patent No.: US 8,080,706 B2
(45) Date of Patent: *Dec. 20, 2011

(54) ISOLATED NUCLEIC ACIDS ENCODING AUTOACTIVATED RESISTANCE PROTEINS AND USES THEREOF

(75) Inventor: Dietmar Juergen Stahl, Einbeck (DE)

(73) Assignee: KWS Saat AG, Einbeck (DE)

( * ) Notice: Subject to any disclaimer, the term of this patent is extended or adjusted under 35 U.S.C. 154(b) by 590 days.

This patent is subject to a terminal disclaimer.

(21) Appl. No.: 11/916,086

(22) PCT Filed: Jun. 2, 2006

(86) PCT No.: PCT/DE2006/000950
§ 371 (c)(1),
(2), (4) Date: Nov. 30, 2007

(87) PCT Pub. No.: WO2006/128444
PCT Pub. Date: Dec. 7, 2006

(65) Prior Publication Data
US 2009/0300795 A1 Dec. 3, 2009

(30) Foreign Application Priority Data
Jun. 3, 2005 (DE) .................. 10 2005 026 045

(51) Int. Cl.
*A01H 5/00* (2006.01)
*A01H 5/10* (2006.01)
*C12N 15/09* (2006.01)
*C12N 15/82* (2006.01)

(52) U.S. Cl. ........ 800/279; 800/278; 800/298; 800/295; 536/23.6; 435/69.1; 435/468

(58) Field of Classification Search .................. None
See application file for complete search history.

(56) References Cited

FOREIGN PATENT DOCUMENTS
WO 01/29239 A2 4/2001

OTHER PUBLICATIONS

Huang et al. Accession No. AY849382, Deposited Apr. 14, 2005.*
Fourgoux-Nicol et al (1999), Plant Molecular Biology 40: 857-872.*
Abdelhafid Bendahmane et al. "Constitutive gain-of-function mutants in a nucleotide binding site-leucine rich repeat protein encoded at the Rx locus of potato" Plant Journel, vol. 32, No. 2, pp. 195-204, Oct. 2002.
M Seki et al. "*Arabidopsis thaliana* cDNA clone:RAFL09-20-MOB, 5' -end" Database EMBL XP002411224 Database accession No. ZV827853 Mar. 2003.
Blake C Meyers et al. "Genome-wide analysis of NBS-LRR-encoding genes in *Arabidopsis* ." Plant Cell, vol. 15, No. 4, pp. 809-834 Apr. 2003.
Donna Frost et al. "Tobacco Transgenic for the Flax Rust Resistance Gene L Expresses Allele-Specific Activation of Defense Responses." Molecular Plant-Microbe Interactions, vol. 17, No. 2, pp. 224-232 Feb. 2004.

Gynheung An "Binary Ti Vectors for Plant Transformation and Promoter Analysis" Methods in Enzymology, vol. 153, pp. 292-305.
Amos Bairoch et al. "The PROSITE database, its status in 1995" Nucleic Acids Research, vol. 24, No. 1, pp. 189-196 (1996).
Agim Ballvora et al. "The R1 gene for potato resistance to late blight (*Phytophthora infestans*) belongs to the leucine zipper/NBS/LRR class of plant resistance genes" The Plant Journal, vol. 30(3), pp. 361-371, (2002).
Abdelhafid Bendahmane et al. "Constitutive gain of function mutants in nucleotide binding site-leucine rich repeat protein encoded at the Rx locus of potato" The Plant Journal, vol. 32, pp. 195-204, (2002).
Jacek Hennig et al. "Pathogen, salicylic acid and developmental dependent expression of a β-1,3-glucanase/GUS gene fusion in transgenic tobacco plants" The Plant Journal, vol. 4(3), pp. 481-493, (1993).
Paul Howles et al. "Autoactive Alleles of the Flax L6 Rust Resistance Gene Induce Non-Race-Specific Rust Resistance Associated with the Hypersensitive Response" Molecular Plant-Microbe Interactions, vol. 18, No. 6, pp. 570-582, (2005).
Sanwen Huang et al. "Comparative genomics enabled the isolation of the R3a late blight resistance gene in potato" The Plant Journal, vol. 42, pp. 251-261, (2005).
Keith Lindsey et al. "Regeneration and transformation of sugarbeet by *Agrobacterium tumefaciens*" Plant Tissue Culture Manual, vol. B7, pp. 1-13, (1991).
Andrei Lupas et al. "Predicting Coiled Coils from Protein Sequences" Science, vol. 252, pp. 1162-1164, (1991).
Gregory B. Martin et al. "Understanding the Functions of Plant Disease Resistance Proteins" Annu. Rev. Plant Biol., vol. 54, pp. 23-61, (2003).
Norbit Martini et al. "Promoter sequences of a potato pathogenesis-related gene mediate transcriptional activation selectively upon fungal infection" Mol Gen Genet, vol. 236, pp. 179-186, (1993).
Giles E. D. Oldroyd et al. "Genetically engineered broad-spectrum disease resistance in tomato" Proc. Natl. Acad. Sci., vol. 95, pp. 10300-10305, Aug. 1998.
Paul J Rushton et al. "Synthetic Plant Promoters Containing Defined Regulatory Elements Provide Novel Insights into Pathogen- and Wound-Induced Signaling" The Plant Cell, vol. 14, pp. 749-762, Apr. 2002.
Deborah A. Samac et al. "Developmental and Pathogen-Induced Activation of the *Arabidopsis* Acidic Chitinese Promotor" The Plant Cell, vol. 3, pp. 1063-1072, Oct. 1991.
Klaus Schmidt et al. "Suppression of phenylalanine ammonia lyase expression in sugar beet by the fungal pathogen *Cercospora beticola* is mediated at the core promoter of the gene" Plant Molecular Biology, vol. 55, pp. 835-852, (2004).
Erik L. L. Sonnhammer et al. "Pfam: A Comprehensive Database of Protein Domain Families Based on Seed Alignments" Proteins: Structure, Function, and Genetics, vol. 28, pp. 405-420, (1997).

(Continued)

*Primary Examiner* — Medina A Ibrahim
(74) *Attorney, Agent, or Firm* — Patent Central LLC; Stephan A. Pendorf

(57) ABSTRACT

The invention relates to nucleic acid, which codes for an autoactivated resistance protein for creating a resistance to pathogens in plants, characterized in that the nucleic acid has a limited portion of an NBS-LRR resistance gene, which extends from the 5'-end of the coded region of the NBS-LRR resistance downstream to the beginning of the NBS domain of the NBS-LRR resistance gene, the NBS-LRR resistance gene not being a TIR-NBS-LRR resistance gene.

24 Claims, 24 Drawing Sheets
(24 of 24 Drawing Sheet(s) Filed in Color)

OTHER PUBLICATIONS

Xiaoyan Tang et al. "Overexpression of Pto Activates Defense Responses and Confers Broad Resistance" The Plant Cell, vol. 11, pp. 11-29, Jan. 1999.

Yanyan Tian et al. "The Absence of TIR-Type Resistance Gene Analogues in the Sugar Beet (*Beta vulgaris* L.) Genome" Journal of Molecular Evolution, vol. 58, pp. 40-53, (2004).

Thomas W. Traut "The funtions and consensus motifs of nine types of peptide segments that form different types of nucleotide-binding sites" Eur. J. Biochem, vol. 222, pp. 9-19, (1994).

Gynheung An "Binary Ti Vectors for Plant Transformation and Promoter Analysis" Methods in Enzymology, vol. 153, pp. 292-305, 1987.

* cited by examiner

```
                    1                                                          50
Bv12069      (1) ------M███████MVTKTTLAH██TP█GD█TCSYATQGILAAQGVRND█
Bv13033_#159 (1) ---MEF█ST█SI█ERLNTALQ█WEFKDK█FSNFS----------YSTE█
BvKWS3_135_#147 (1) -------M██████VF█ER██DV█QE█GV█LG----------PKDR█
BvKWS3_165-#175 (1) ---MVIGC█IT█F█QV██EK█SG█ISL█FLRERG------IGPKV█
R3a-#1-155   (1) MEIGLA█GT█L██A█NV█DR██PH█DL█NMFQKHK------DRVKL█
Consensus    (1)       M EAVLSA L  LF LA G  L                        LK
                    51                                                         100
Bv12069      (45) █NK█IA█P██Q█ES█YDS██A██Y██V█I█
Bv13033_#159 (39) █PT█SG█T█RV█T█LELS█I█RQ█P█H██V█L
BvKWS3_135_#147 (33) █ND█KY█L█FK█ERL█RKD██CT█A████A█QLL
BvKWS3_165-#175 (42) █KK█PL█S█SL█EQ█FHN██A█I██F█A█I█
R3a-#1-155   (45) █DI█LG█CI█S█N█ASN█H█QF█N█I█A█D█P█A█T█
Consensus    (51) KLQ   L   I AVL DAE KQ    SAVK WL DLKE VTDAEDLLDEV  TD
                    101                                                        150
Bv12069      (95) LLRK█████HLLRQIRYYLS-------SSNP█LSN█WS-------U█
Bv13033_#159 (89) █HQQ██VD█DGS█L█KVRHFFS-----SSNP█CVS█S-------RG
BvKWS3_135_#147 (83) ------█GKL█R█YSPTK---------PAK█IG-------K█
BvKWS3_165-#175 (92) █RLKE██D█PQPQP█EHQPKSSCSPFNKVQSC█SCG█PTLNKETTKYST█
R3a-#1-155   (95) █LRL██FG█HQN█A█PSNQQ-----VSDLNLC█SDD██N------IKE█
Consensus    (101) A    RVN S    L D                 I    FFM             K
                    151                                                190
Bv12069      (129) ██VQ█████AA█KKD██DQHDPIEVYNI█RNPLDA--
Bv13033_#159 (125) SR█KK████AN█NQFS█ELDHEPIRNRP█FCS-----
BvKWS3_135_#147 (108) █DE████KN█SAF█GPLQPVHGNVEE█GPPKWSSP
BvKWS3_165-#175 (142) █ST████LI█RS█T█STQIHSRVEQH█ER-----
R3a-#1-155   (134) █TIE█████EX█GP███TS--------------
Consensus    (151) I  SI   KLDDI  NI LLL              S
```

Fig. 10c the market, US 8,080,706 B2

SEQUENCE LISTING

<160> NUMBER OF SEQ ID NOS: 21

<210> SEQ ID NO 1
<211> LENGTH: 660
<212> TYPE: DNA
<213> ORGANISM: Beta vulgaris

<400> SEQUENCE: 1

```
gaattcgagc tccaccgcgg gattctaata cgactcacta tagggcaagc agtggtatca      60
acgcagagta cgcggrgatt catactctac ttccatactt tgtaaaaaca aaaaagata      120 aaaatggtga taggcggaga gattttttcta tcagcgtttc ttcaagtgct ctttgaaaag    180
cttgcatcag gagggataag tctattccta aaaagagaaa aaggaatagg acctaaagtt    240
attcaaagat ggaacaaaaa attgagatta atagaggcgg ttttaagtga cgccgagcaa    300
aagcagtttc acaacaatgc cgtcaaattg tggcttcgag atcttcaaga gttcgcgtac    360
gatttagagg acatcttaga cgaatttgat acagatgctc gacttaagga gttcaatgat    420
cagcctcagc cacagccaca ggaacatcaa cccaaatctt cttgttctcc tttcaataag    480
gtacaaagct gtctttcttg tggtttccca actttaaata agaaaactac aaagtattca    540
actagcattg aagagatgag cactcgcttg gaagatcttc tggaccaagt aaggtctttg    600
gctctctcaa cgcagataca ctcaagggta gagcaacatg aagaacggag gtgaggatcc    660
```

<210> SEQ ID NO 2
<211> LENGTH: 604
<212> TYPE: DNA
<213> ORGANISM: Beta vulgaris

<400> SEQUENCE: 2

```
gaattcgagc tccaccgcgg gattctaata cgactcacta tagggcaagc agtggtatca      60
acgcagagta cgcggggaat ttgaagtcat catcaacctc ttatcatcat ccaactccaa    120
gattctctca tcactgacag ttctggagta gaatatggtg gacgcagtgg tcactgtgtt    180
tttggaaaaa cttttcaatg tccttgttca ggagggtggt gttttacttg gtttcaaaga    240
tcggtttaag aagctacaaa atgatctcaa atacatgcaa agcttcttta aagacgccga    300
gaggctcaaa aggaaagatg agtctctaaa atgcactctg gccgacatgc gtgagctggt    360
atatgaagct gaagacatac ttgcagattg ccagcttttg tcaaatagtt ctggaaaact    420
tcttgaagac tattctccta caaaggttcc agccaaatat caaatgggga aaagaattgg    480
tgaaatcaat gaaaagatca atagcattaa aaataacatc tcagcttttc ttgggcctct    540
tcaacctgtc catggtaatg tagaagaaga gggaccaccc agatggagtt ctccctgagg    600
atcc                                                                  604
```

<210> SEQ ID NO 3
<211> LENGTH: 580
<212> TYPE: DNA
<213> ORGANISM: Beta vulgaris

<400> SEQUENCE: 3

| | | | | | | |
|---|---|---|---|---|---|---|
| gaattcgagc | tccaccgcgg | acgcgtgggc | agcagccaaa | cacacactt | ctctcctgat | 60 |
| catcaatcat | cattatcatc | tccaaaacca | aaaatggaat | tcataagcac | aacagtctct | 120 |
| atcgctgaaa | aactgaatac | tgcactgcag | ttatgggagt | tcaaagacaa | gctctttagt | 180 |
| aacttcagct | acgaaaccga | acttgaggat | ctccaacgca | ccgtcagttc | cataactgcg | 240 |
| gcgctacatg | tagcagagac | caagctggag | ctctccgatg | aactacaacg | tcaaatcgag | 300 |
| gagctcaagg | ataccatctt | tgaagcggat | gatctactgg | atgagcttgt | cactctttct | 360 |
| caccagcagc | gggttgtaga | tgccgatggt | agtctcctag | ataaagtaag | acacttcttc | 420 |
| tctagttcca | acccaatctg | tgtttcttac | tggatgtctc | gggggagtaa | ggatatcaag | 480 |
| aagaaattag | atgatattgc | taacaataat | cagtttagct | tagagcttga | tcatgagcct | 540 |
| atcaggaaca | gaaggcctga | gacttgttct | tgaggatcct | | | 580 |

<210> SEQ ID NO 4
<211> LENGTH: 2047
<212> TYPE: DNA
<213> ORGANISM: Beta vulgaris

<400> SEQUENCE: 4

| | | | | | | |
|---|---|---|---|---|---|---|
| agtttgtaca | aaaaagcagg | ctggtaccgg | tccggaattc | ccgggatatc | gtcgacccac | 60 |
| gcgtccgctt | caacaaccca | tctcttcaat | aattgtgaaa | aaccacaaat | catgattaag | 120 |
| taatttctgc | accactttg | catcctcagc | cccttctaaa | tccttccccc | tgaagtgatc | 180 |
| aataatcatt | agaatgtctg | aagcactact | gtgggctgtc | acaaaaacaa | cacttgcaca | 240 |
| cattgctact | tttgctggtg | atcttacctg | cagttatgct | acacaaggca | ttttagcagc | 300 |
| tcaaggtgtc | cgaaacgacc | tcaaaaagat | cgagaacaag | ctgattgcta | ttcgcgctgt | 360 |
| tctgcaagat | gcagaaagta | agcaatatga | tagcgaggct | gtcaagattt | ggctgaaaga | 420 |
| tgtcaaaaat | gttgtgtatg | atatagatga | cctcttggat | gaagttcaca | ctgatctgtt | 480 |
| acgaaagaga | atcaacaaaa | gccatctgct | tcgacaaatc | aggtactatc | tttcatcctc | 540 |
| gaatccaatt | ctgagtaatt | tttattggag | tgataagatt | agagaccttg | ttcaaagatt | 600 |
| tgatgacatt | gctgctaata | gacgagatct | tggattggat | ggtcatgatc | caattgaagt | 660 |
| atacaacatt | gagaggaatc | ctttagatgc | ataatcatat | gtgaagaaat | cagaaattat | 720 |
| tggtagagat | gaagctaggt | ccgaaataat | tagacgctta | actagtagta | ctagtgttgg | 780 |
| agatgctagt | aggttggttg | tgcttccgat | agttgggttt | ggcgggattg | ggaaaacagc | 840 |
| attggcaaag | cttgttttta | atgatgagtg | ggttgctagt | aactttgata | ttaagttgtg | 900 |
| ggcatgtgtc | tctgaaaaat | ttgatctgca | gaagactaca | gaagaaattt | tgaattctgt | 960 |
| aagtaatgaa | accactgcaa | acctcaacat | gagacagttg | catgaaaaac | tccgtgagat | 1020 |
| attggatgat | cggaagcatt | tccttgtgct | ggacaatgtg | tggatcgagg | acatcaaagt | 1080 |
| gcactccaca | ggaagcattt | ccttgtactg | gcatttagag | agggtgaaga | aacaagatac | 1140 |
| ccaaagcttg | ctacaatcgg | gaaaagcatt | gttgaaaatt | gtggcggggt | tcctctggtt | 1200 |
| gttaaggttc | ttgcaagcct | gttacacagt | gaaaggaacg | agaaagaatg | gaggcgaatt | 1260 |
| tctgaaacaa | acaacataat | gatatcaaac | aagctttgag | agtgagctac | aataaactcc | 1320 |

-continued

```
catctcaatt aaaagcatgt ttttcctatt gttcattatt tgtgaaggat agcaagctta   1380
atcctccgat tttgtcatgc ctgtggagtg cacttggaat cttgcaacga ggtaacgaca   1440
atgaagagtt ataatccatt ggatacaagt attgtgaaga cctatagtca agatgtcttc   1500
ttcaggatgc atttcttgtg ttcaccgaaa ttataagtga atgtagaatg cacgacttat   1560
tccatgattt agcaactgac cttgttggtg aagagatagc tgttgtgacc agtaatcatc   1620
ttaatgtttc agatatgtgc aggcatttag tatggggata tgaaggaggt gaaggtttat   1680
cagataagaa tttcccaaaa gagctactta gagcaaagaa ggctcgaact ttcagatttg   1740
gctatgcaat gggctatatt agcaagtcat ttattgaaag tattatacac aacttcaggt   1800
gcttacgtgt gttggatttg cattagagta gcttcgagga gttgtcgatg tcaattggga   1860
agttagaaca tctaagatat cttgacctgt cctacaaccc aatcatcaaa tttcttccaa   1920
gtacactatg caagttgttg aatctacaat cgttgtatgt tccaaaaaaa aaaaaaaagg   1980
gcggccgctc tagagtatcc ctcgaggggc ccaagcttac gcgtacccag ctttcttgta   2040
caaagtg                                                             2047
```

<210> SEQ ID NO 5
<211> LENGTH: 3463
<212> TYPE: DNA
<213> ORGANISM: Beta vulgaris

<400> SEQUENCE: 5

```
gattcatact ctacttccat actttgtaaa aacaaaaaaa gataaaaatg gtgataggcg     60
gagagatttt tctatcagcg tttcttcaag tgctctttga aaagcttgca tcaggaggga    120
taagtctatt cctaaaaaga gaaaaggaa taggacctaa agttattcaa agatggaaca    180
aaaaattgag attaatagag gcggttttaa gtgacgccga gcaaaagcag tttcacaaca    240
atgccgtcaa attgtggctt cgagatcttc aagagttcgc gtacgattta gaggacatct    300
tagacgaatt tgatacagat gctcgactta aggagttcaa tgatcagcct cagccacagc    360
cacaggaaca tcaacccaaa tcttcttgtt ctccttttcaa taaggtacaa agctgtcttt    420
cttgtggttt cccaacttta aataagaaaa ctacaaagta ttcaactagc attgaagaga    480
tgagcactcg cttggaagat cttctggacc aagtaaggtc tttggctctc tcaacgcaga    540
tacactcaag ggtagagcaa catgaagaac ggagggaaac atcatctatg atacgggagc    600
cagttgtata tgggagggac gatgagaaaa atcagataat ccaaagatta ttaaagacag    660
atgagccatt ttgtgaaaat tacaatgtaa ttcctattgt tggaacagga ggcattggga    720
agacgaccct cgctcaggct gtatacaatg atgagcaggt gaaggctcac tttgatgtaa    780
aagcatgggt gtgcatctcc gatgagtttg atgtcaaaca agtgacaaca agcattatca    840
cttcagccac tcgtgataca tgtaatttcg gtgttctaga tgaggcacaa gataaattaa    900
agaacttgct tgtagacaaa agattcttga tcgttcttga tgatatatgg agtgatgaat    960
atgatccttg ggaccaactt caaaccccctt tttcatcagc gaagaaggga agtagagttc   1020
taatcacgac cagaatggag acggtggcaa agaacatggt taaaagacca gatcaaagcc   1080
ccatcatcaa gttaaaggtt ttatctgatg atgattgttg gcttctcttt caaaagcatg   1140
cagtcgtaga tgaagacctc attgtgatgc agaaggactt ggttgggttg ttcaaaggat   1200
tgcctttggc tgcaaaagct ctaggaggtc tcctaaggag agagcgtaag agtaattggg   1260
caaggatatt aaagagcaat atttggagtg aagaaggtgg tgttctgcca gtcttgaggc   1320
ttagttatca tcatctccca caaaacctca acgtgccctt tgcttattgt tctatattcc   1380
```

-continued

```
cgaaagatta taaattcacg gagatgaatg ttatattaat gtggatagca gaaggcttgc    1440
tgccagagca cgacaaggag tgcaaggaag acattggtcg tgactatttt cttgatctag    1500
tatcaagatc attgtttgaa ccaaacagtc caatgtatat ggatggatct ttcattatgc    1560
atgacctaat ccatgaccta gctcaatggg ctgctggtga agtttgttgc acattgaata    1620
tccaaaaact ttcttctaga acacgttatt ggtctttctc tgaagaaata ctgatagatc    1680
aaacatggac ttcaaagaaa cttgtccagg tacgatcatt tgcttctttt ggtgcattag    1740
atgttcgaat tcctatgcaa ctactagatt ccattttccg tcagtttcaa tacttacgct    1800
tgttgcgtat gcataaggcg ggaataattg agttaccaaa tagtatgggt aatctgaaac    1860
acttgagact tcttgacctc tcatggaata caaaactaac tagattgcca agtccacta    1920 gcaagctttg caacctccag acgctgctgt taagaggatg taagtctctt gtggagatag    1980
tccctctaat cgaacttcaa caccttgatg ttagtagtag gtatgctgct tcaccgttgg    2040
ggattggaaa attaacaaac ttgcagacat tgaagggatt tactttgaga agatactcta    2100
agacaagtat aagtgaattg aagaacttga atgcctccg tggctcactg gacatccatg    2160
gcctagagaa tgtgtttagt agtgaagaag cacaagcagc aaggttgcac gaaaagacag    2220
gccttgataa gttggaaatg tattggggag ataatgccca tgatgttgat gacaacatta    2280 aaaagatgt agttgatcga ttacagcctc cggaatccat caagaattag acgttgaatg    2340
ggtacgacgg cttaacattc cctgcttggt tgggaaatcc ctcttacact aatatggttt    2400
tcatagaatt aagggagtgt aggagatgtg aattcttacc agcactaggg cagctgccct    2460
cattaaagaa catcataata gaagggatgg atgatattaa gactgtaggc cctgaatttt    2520
acggcaatga tgatggttgt tcaaacctgt ttcctgcatt gaaaagtcta cgattctatg    2580 gaatggggg ttgggaggag tggttggccc catcagttga caatagcaat gcatttccct    2640
gccttgaata tattagcata tatgaatgtc cattgttgcg ggctaactta ccttcccatc    2700
tcccatccct aaaagacttg tccattggca aatgcaaaga gttgagattg tcacttccaa    2760 gctgccctt gctccaaaaa ttgactatta aacatatga gacgccattt agtattgctg    2820
attgtttgcc ctcaactctt gagaccctgg aaatcttgca ctccgaaaata gagcagccaa    2880 ttcaagagtg gaaacttgac ctccttactt ctcttaaatc tcttgatctc caaaacatag    2940
gcagagccgc agatacaata gagcatattc cccaaccaga ttttcatctt ccctcttcct    3000
tgtcttcctt atatatctcg gatttcaaga atttgaaatc cttgtcatgc tctacccttc    3060
ccaacctcac tgaaattaaa atctggaatt gtaagaagct ggaatcattg ggtgtcgatt    3120
tcccaccatc gaagcttcag gaagcgtatt ttagtgattg ccctttgatt tatcaacgat    3180
gcaaccggaa tccccatgga cttattgttt taattatat tgataaatac aaatattcgt    3240
acatttgaag attccagttt tcattccctg aagattgagt tggaggtgga gttttggggt    3300
ttttttcaga ttttgttttt gttttttttc attttcttta gttatttgt atgaaactag    3360 aatatattca aggaattgtg ataaaaaaaa aaaaaaagg gcggccgctc tagagtatcc    3420 ctcgagggc ccaagcttac gcgacccagc tttcttacaa agg                      3463
```

<210> SEQ ID NO 6
<211> LENGTH: 24
<212> TYPE: DNA
<213> ORGANISM: Petroselinium crispum

<400> SEQUENCE: 6
cagccaccaa agaggaccca gaat    24

<210> SEQ ID NO 7
<211> LENGTH: 29
<212> TYPE: DNA
<213> ORGANISM: Petroselinium crispum

<400> SEQUENCE: 7
ttattcagcc atcaaagttg accaataat                                    29

<210> SEQ ID NO 8
<211> LENGTH: 31
<212> TYPE: DNA
<213> ORGANISM: Petroselinium crispum

<400> SEQUENCE: 8
tacaattcaa acattgttca acaaggaac c                                  31

<210> SEQ ID NO 9
<211> LENGTH: 25
<212> TYPE: DNA
<213> ORGANISM: Solanum tuberosum

<400> SEQUENCE: 9
ttctagccac cagatttgac caaac                                        25

<210> SEQ ID NO 10
<211> LENGTH: 141
<212> TYPE: DNA
<213> ORGANISM: Artificial Sequence
<220> FEATURE:
<223> OTHER INFORMATION: combination of cis-elements 2xS-2xD from
      parsley

<400> SEQUENCE: 10
actagtcagc caccaaagag gacccagaat tctagtcagc caccaaagag gacccagaat    60
tctagttaca attcaaacat tgttcaaaca aggaacctct agttacaatt caaacattgt   120
tcaaacaagg aacctctaga g                                            141

<210> SEQ ID NO 11
<211> LENGTH: 150
<212> TYPE: DNA
<213> ORGANISM: Artificial Sequence
<220> FEATURE:
<223> OTHER INFORMATION: combination of cis-elements 2xW2-2xD from
      parsley

<400> SEQUENCE: 11
actagtttat tcagccatca aagttgacca ataattctag tttattcagc catcaaagtt    60
gaccaataat tctagttaca attcaaacat tgttcaaaca aggaacctct agttacaatt   120
caaacattgt tcaaacaagg aacctctaga                                   150

<210> SEQ ID NO 12
<211> LENGTH: 142
<212> TYPE: DNA
<213> ORGANISM: Artificial Sequence
<220> FEATURE:
<223> OTHER INFORMATION: combination of cis-elements 2xGst 1-2xD from
      potato and parsley

<400> SEQUENCE: 12
actagtttct agccaccaga tttgaccaaa ctctagtttc tagccaccag atttgaccaa    60
actctagtta caattcaaac attgttcaaa caaggaacct ctagttacaa ttcaaacatt   120
gttcaaacaa ggaacctcta ga                                           142

<210> SEQ ID NO 13
<211> LENGTH: 36
<212> TYPE: PRT
<213> ORGANISM: Artificial Sequence
<220> FEATURE:
<223> OTHER INFORMATION: consensus sequence of two organisms Beta
      vulgaris and Solanum tuberosum; Xaa = any of the 20 natural amino
      acids
<220> FEATURE:
<221> NAME/KEY: MISC_FEATURE
<222> LOCATION: (4)..(4)
<223> OTHER INFORMATION: xaa = each of the 20 amino acids
<220> FEATURE:
<221> NAME/KEY: MISC_FEATURE
<222> LOCATION: (8)..(8)
<223> OTHER INFORMATION: xaa = each of the 20 amino acids
<220> FEATURE:
<221> NAME/KEY: MISC_FEATURE
<222> LOCATION: (11)..(15)
<223> OTHER INFORMATION: xaa = each of the 20 amino acids
<220> FEATURE:
<221> NAME/KEY: MISC_FEATURE
<222> LOCATION: (17)..(18)
<223> OTHER INFORMATION: xaa = each of the 20 amino acids
<220> FEATURE:
<221> NAME/KEY: MISC_FEATURE
<222> LOCATION: (21)..(21)
<223> OTHER INFORMATION: xaa = each of the 20 amino acids
<220> FEATURE:
<221> NAME/KEY: MISC_FEATURE
<222> LOCATION: (26)..(26)
<223> OTHER INFORMATION: xaa = each of the 20 amino acids
<220> FEATURE:
<221> NAME/KEY: MISC_FEATURE
<222> LOCATION: (30)..(30)
<223> OTHER INFORMATION: consensus sequence of two organisms sugar beet
      and potato; xaa = each of the 20 amino acids

<400> SEQUENCE: 13

Ala Val Leu Xaa Asp Ala Glu Xaa Lys Gln Xaa Xaa Xaa Xaa Xaa Leu
1               5                   10                  15

Xaa Xaa Trp Leu Xaa Asp Leu Lys Asp Xaa Val Tyr Asp Xaa Asp Asp
                20                  25                  30

Ile Leu Asp Glu
        35

<210> SEQ ID NO 14
<211> LENGTH: 11
<212> TYPE: PRT
<213> ORGANISM: Artificial Sequence
<220> FEATURE:
<223> OTHER INFORMATION: consensus sequence of two organisms (Beta
      vulgaris and Solanum tuberosum); Xaa = any of the 20 natural amino
      acids
<220> FEATURE:
<221> NAME/KEY: MISC_FEATURE
<222> LOCATION: (2)..(2)
<223> OTHER INFORMATION: xaa = any of the 20 natural amino acids
<220> FEATURE:
<221> NAME/KEY: MISC_FEATURE
<222> LOCATION: (5)..(6)
<223> OTHER INFORMATION: xaa = any of the 20 natural amino acids

<400> SEQUENCE: 14

Ile Xaa Glu Ile Xaa Xaa Lys Leu Asp Asp Ile
1               5                   10

<210> SEQ ID NO 15
<211> LENGTH: 99
<212> TYPE: PRT
<213> ORGANISM: Artificial Sequence
<220> FEATURE:

```
<223> OTHER INFORMATION: consensus sequence of two organisms (Beta
      vulgaris and Solanum tuberosum)
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (37)..(88)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (93)..(94)
<223> OTHER INFORMATION: Xaa can be any naturally occurring amino acid

<400> SEQUENCE: 15

Ala Val Leu Xaa Asp Ala Glu Xaa Lys Gln Xaa Xaa Xaa Xaa Xaa Leu
1               5                   10                  15

Xaa Xaa Trp Leu Xaa Asp Leu Lys Asp Xaa Val Tyr Asp Xaa Asp Asp
            20                  25                  30

Ile Leu Asp Glu Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Ile Xaa Glu Ile Xaa Xaa Lys Leu
                85                  90                  95

Asp Asp Ile

<210> SEQ ID NO 16
<211> LENGTH: 468
<212> TYPE: DNA
<213> ORGANISM: Beta vulgaris

<400> SEQUENCE: 16
atggagattg gcttagcagt tggtggtgca tttctctctt cagctttgaa tgttctcttt       60
gataggcttg ctcctcacgg tgatctgctc aacatgtttc agaagcataa ggatcatgtt      120
aagctcttaa agaagctgga ggacattttg ctcggtcttc agattgtgct aagtgatgca      180
gagaataaac aagcatcaaa tcgacatgtg agccagtggt tcaataagct tcagaatgct      240
```

```
gtggacggtg ctgagaactt gatagaacaa gtcaattatg aagctttgag gcttaaggtg    300
gaaggccagc atcaaaatct tgcagaaaca agcaaccagc aagtaagtga ccttaacctg    360
tgcttcagtg atgatttctt tcttaacata aaggataagt tggaagaaac cattgaaaca    420
ttggaggtgt tggaaaagca aattggtcgc cttgtaatca ctagctag                 468
```

```
<210> SEQ ID NO 17
<211> LENGTH: 25
<212> TYPE: DNA
<213> ORGANISM: Beta vulgaris

<400> SEQUENCE: 17
ctcgagaatt cgagctccac cgcgg                                           25

<210> SEQ ID NO 18
<211> LENGTH: 36
<212> TYPE: DNA
<213> ORGANISM: Beta vulgaris

<400> SEQUENCE: 18
ctggatcctc acctccgttc ttcatgttgc tctacc                               36

<210> SEQ ID NO 19
<211> LENGTH: 35
<212> TYPE: DNA
<213> ORGANISM: Beta vulgaris

<400> SEQUENCE: 19
ctggatcctc agggagaact ccatctgggt ggtcc                                35

<210> SEQ ID NO 20
<211> LENGTH: 35
<212> TYPE: DNA
<213> ORGANISM: Beta vulgaris

<400> SEQUENCE: 20
ctggatcctc aagaacaagt ctcaggcctt ctgtt                                35

<210> SEQ ID NO 21
<211> LENGTH: 7
<212> TYPE: PRT
<213> ORGANISM: Artificial Sequence
<220> FEATURE:
<223> OTHER INFORMATION: Particularly good autoactivation is possible
      with nucleic acids that code for the sequence motif AVLXDAE.  This
      sequence is found, for example, in SEQ ID NOs: 13 and 15.
<220> FEATURE:
<221> NAME/KEY: misc_feature
<222> LOCATION: (4)..(4)
<223> OTHER INFORMATION: Xaa can be any naturally occurring amino acid

<400> SEQUENCE: 21

Ala Val Leu Xaa Asp Ala Glu
1               5
```

ISOLATED NUCLEIC ACIDS ENCODING AUTOACTIVATED RESISTANCE PROTEINS AND USES THEREOF

CROSS REFERENCE TO RELATED APPLICATIONS

This application is a §371 National Phase of PCT/DE2006/000950, filed Jun. 2, 2006. This application claims the benefit of German Application No. DE 10 2005 026 045.4, filed Jun. 3, 2005.

BACKGROUND OF THE INVENTION

The present invention concerns a nucleic acid which codes for an autoactivated resistance protein for generating a resistance to pathogens in plants, the use of the nucleic acid for producing a transgenic plant as well as transgenic plants.

Plant diseases caused by fungi, virus, nematodes and bacteria cause large losses to harvest worldwide, compromise the quality of the harvested products and necessitate the costly and laborious application of chemical pesticides, since the natural defense mechanism of plants to fend against or delay and curb the spread the majority of potential pathogens frequently do not suffice. These defense mechanisms include hypersensitive reactions, the controlled cellular death of the host tissue at the infection site, the strengthening of the plant cell wall by lignification and callus formation, the formation of phytoalexins and the production of PR-(pathogenesis-related) proteins. The plant resistance genes (R-genes) are key molecules for the activation of the induced defense mechanisms. According to Flohr's gene-for-gene postulate the protein of an R-gene interacts with a corresponding protein of a microbial avirulence gene (Avr-gene) and thereby triggers the induced defensive reaction.

The majority of the R-genes can be categorized into five classes corresponding to the structure of the R-proteins for which they code (Martin et al, 2003). Class 1 includes only the Pto-gene of the tomato, which codes for a serin/threonine-kinase. The majority of the plant R-genes however belong to the superfamily NBS-LRR-genes, which code for a "nucleotide biding site" (NBS) and a "leucine rich repeat" (LRR). NBS-LRR-genes which exhibit on their N-terminus a "coiled-coil"-structure (CC) such as, for example, a "leucine zipper", are categorized as CC-NBS-LRR-genes of Class 2. R-genes of CC-NBS-LRR-type are found in all angiosperms. Class 3 includes the R-genes of TIR-NBS-LRR-type, which carry on the N-terminus in place of a C-domain a sequence with homology to the animal TIR-region ("toll-interleukin-1-receptor"). Although the TIR-NBS-LRR-genes comprise approximately 75% of the R-genes in *Arabidopsis thaliana*, they are however not found in grasses nor in sugar beets (Tian et al., 2004).

The fourth class of the R-genes is formed by the Cf-gene of the tomato. CF-proteins have no NBS-domain, however a transmembrane domain (TM) and an extracellular LRR. The fifth class includes the Xa21-protein from rice, which is constructed from an extracellular LRR-domain, a transmembrane-domain and an intracellular kinase-domain.

While R-genes are only weakly expressed by the R-gene promoters, a strong, constitutive expression of R-genes of Classes 1, 2 and 3 results in an activation of the plant pathogen defense mechanism even in the absence of a corresponding avirulence gene product and therewith in autoactivation of the R-protein (Tang et al., 1999; Oldroyd and Staskawicz, 1998; Bendahmane et al., 2002).

Generally however the constitutive overexpression of R-genes in transgenic plants is associated with agronomically undesired characteristics, such as micronecrosis (Tang et al., 1999) or dwarfism of the plants (Frost et al., 2004).

A further possibility of the autoactivation of R-proteins of Classes 2 and 3 is the mutagenesis of special, conserved amino acid motifs in the complete CC-NBS-LRR or, as the case may be, TIR-NBS-LRR proteins. The mutagenesis of sequences in the NBS- or, as the case may be, LRR domains of the Rx-gene of the potato (Bendahmane et al., 2002) and the NBS-domains of the L6-gene of flax (Howles et al., 2005) results in mutants, which, in the absence of the corresponding avirulence gene, after transient expression, initiate cell death.

Deletion experiments with the Rx-gene show that deletion products comprised of the CC-domains and parts of the NBS-domain likewise can trigger a cell death after their transient overexpression, which occurs more rapidly than in the case of use of the full-length R-gene. These deletion products require, besides the CC-domains, also the P-loop, the kinase-2 and the complete kinase-3a of the NBS-domains. In contrast, a further shortening of the NBS-domain leads to a slower HR-triggering or initiation in comparison to the compete R-gene (Bendahmane et al. 2002).

An autoactivation of the L10-gene of flax, a R-gene of Class 3, could be achieved by formation of a shortened TIR-NBS-LRR-protein, which was comprised of TIR-domains and 34 amino acids of the restricted NBS-domain inclusive of the P-loop (Frost et al., 2004).

Although multiple methods of autoactivation of R-genes are known, until now no transgenic plants have been described in which the autoactivation of R-proteins leads to an elevated fungal resistance without simultaneously detracting from the agronomic characteristics. Attempts to stably transform two autoactivated full-length variants of the L6-gene respectively under the control of the native L6-resistance gene promoter or a fungus induced promoter in flax resulted either in normal growth fungal susceptible or to dwarf fungal resistant plants (Howels et al., 2005).

BRIEF SUMMARY OF THE INVENTION

It is thus the task of the present invention to so modify the defensive capability of a plant against pathogens, so that the defense reaction of the plant can be reliably activated following pathogen attack, without however negatively influencing the agronomic characteristics of the plants.

In accordance with the invention the set task is solved by a nucleic acid, which includes a limited part of a NBS-LRR-resistance gene, which extends from the 5' end of the coded area of the NBS-LRR-resistance gene downstream to the beginning of the NBS-domain of the NBS-LRR-resistance gene, wherein the NBS-LRR-resistance gene is not a TIR-NBS-LRR resistance gene. Such nucleic acids can be isolated from plants or be produced synthetically.

The limited part of the NBS-LRR-resistance gene begins at the start codon for translation (ATG-codon) and extends to the NBS-domain, which is basically characterized by the P-loop (kinase-1a motif). For the function of the inventive part of the NBS-LRR-resistance gene, the P-loop shall not be included. Similarly, other sections of the NBS-LRR-domains of the NBS-LRR-resistance gene should also no longer be present. However, individual nucleotides of the NBS-domain inclusive of the P-loop may remain, as long as they do not interfere with the triggering of the HR.

The term "autoactivated resistance protein" is understood to mean such a protein, which in the absence of a corresponding avirulence gene product leads to an activation to the plant pathogen defense mechanism. In relationship thereto the invention has the advantage that for formation of a resistance to pathogens no interaction between a resistance protein and an avirulence protein is necessary, whereby the defense reaction of the plant can proceeds substantially more directly and ultimately more reliably.

An autoactivation can occur for example by a transient overexpression of the resistance gene. Overexpression means that the expression strength of the natural R-gene promoter is exceeded to the extent that the signal transduction cascade regulated by the R-protein is activated in the absence of the corresponding microbial avirulence gene product. Thereby, a pathogen defense mechanism is activated, which is manifested by a partial or complete disease resistance.

An autoactivation of the resistance protein can however also be accomplished by shortening the full-length R-gene BvKWS3.sub._165, BvKWS3.sub._135, Bv13033 and Bv12069 of the sugar beet as well as the StR3a gene of the potato to the 5'-area which codes only for the NBS and LRR domain free N-terminus of the protein inclusive of a possible CC-domain. NBS-domain free N-terminus means in this case that the 5'-end of the coded area of the NBS-LRR-resistance gene extends only so far towards the 3'-end, that the P-loop of the NBS-LRR-resistance gene is not included in its effective or operative structure. In the simplest case the P-loop is completely deleted. However individual nucleotides of the P-loop can remain in the shortened resistance gene, to the extent that they do not slow or hinder the triggering of the HR. With the shortening of the NBS-LRR-resistance gene to the N-terminus, also the kinase 2-, kinase 3-, GLPC- and MHD-motif inclusive of the flanking amino acids according to the information of the databank Prosite (Bairoch et al., 1996) and Pfam (Sonnhammer et al., 1997), as well as those motif definitions provided in Bendahmane at al. (2002), are eliminated or removed.

The use of the shortened R-gene 165_#176, 135_#147, 13033_#159 and Bv12069 and StR3a-#1-155 results, in comparison to the full-length R-gene, in a more rapid triggering of cell death in the plant tissue. In combination with a pathogen inducible promoter, an improved induced pathogen defense mechanism can therewith be induced. This applies also for those R-proteins, which cannot be autoactivated by known mutations in the MHD or, as the case may be, VHD domains, which show an expression of the gene 135_#147 and BvKWS3_135-D480V.

Since the shortened R-gene, in comparison to the full-length R-gene, is able to earlier trigger cell death, a smaller expression suffices for the shortened R-gene in order to achieve a critical protein concentration for the pathogen defense mechanism than has been shown for the R-gene 135_#147.

The P-loop or the kinase-1a motif is, together with the kinase-2 and kinase-3 motif, characteristic for ATP or GPT hydrolyzing proteins (Traut, 1994) and is located in the NBS-domains of NBS-LRR-genes. The P-loop characterizes the N-terminal area of the NBS-domain (Bendahmane et al., 2002). The consensus sequence of the P-loop for the R-gene Prf, Rx, Rpm1, BvKWS3_135, BvKWS3_133 and BvKWS3_165 is: (I/V)VG(M/I)GG(L/I/S)GKTT(L/V).

In surprising manner it has been found, that a particularly good autoactivation is possible with nucleic acids which code for an amino acid sequence with a sequence motif DAE. In particular, the nucleic acids code for the sequence motif AVLXDAE. The sequence motif DAE and AVLXDAE are located for example in the SEQ ID NOS: 13 and 15.

Preferred nucleic acid sequences are those from the following groups:

a) nucleotide sequence according to SEQ ID NO: 1 or a nucleotide sequence complimentary to the nucleotide sequence according to SEQ ID NO: 1 or a nucleotide sequence, which hybridizes with the nucleotide sequence according to SEC ID NO: 1 or a nucleotide sequence complimentary to the nucleotide sequence according to SEQ ID NO: 1:

b) nucleotide sequence according to SEQ ID NO: 2 or a nucleotide sequence complimentary to the nucleotide sequence according to SEQ ID NO: 2 or a nucleotide sequence, which hybridizes with the nucleotide sequence according to SEC ID NO: 2 or a nucleotide sequence complimentary to the nucleotide sequence according to SEQ ID NO: 2;

c) nucleotide sequence according to SEQ ID NO: 3 or a nucleotide sequence complimentary to the nucleotide sequence according to SEQ ID NO: 3 or a nucleotide sequence, which hybridizes with the nucleotide sequence according to SEC ID NO: 3 or a nucleotide sequence complimentary to the nucleotide sequence according to SEQ ID NO: 3;

d) nucleotide sequence according to SEQ ID NO: 4 or a nucleotide sequence complimentary to the nucleotide sequence according to SEQ ID NO: 4 or a nucleotide sequence, which hybridizes with the nucleotide sequence according to SEC ID NO: 4 or a nucleotide sequence complimentary to the nucleotide sequence according to SEQ ID NO: 4; and e) nucleotide sequence according to SEQ ID NO: 16 or a nucleotide sequence complimentary to the nucleotide sequence according to SEQ ID NO: 16 or a nucleotide sequence, which hybridizes with the nucleotide sequence according to SEC ID NO: 16 or a nucleotide sequence complimentary to the nucleotide sequence according to SEQ ID NO: 16.

The limited part of the NBS-LRR-resistance gene extends, in the preferred nucleotide gene sequences, as follows:
SEQ ID NO: 1 from Pos. 124-654
SEQ ID NO: 2 from Pos. 155-598
SEQ ID NO: 3 from Pos. 94-573
SEQ ID NO: 4 from Pos. 194-694

The term "hybridized" as used herein means hybridizing under conventional conditions, as described in Sambrook et al. (1989) preferably under stringent conditions. Stringent hybridization conditions are for example: hybridizing in 4×SSC at 65° C. and subsequent multiple washing in 0.1× SSC at 65° C. for a total of approximately 1 hour. Less stringent hybridization conditions are for example: hybridizing in 4×SSC at 37° C. and subsequent multiple washing in 1×SSC at room temperature. "Stringent hybridization conditions" can also mean: hybridizing at 68° C. in 0.25 M sodium phosphate, pH 7.2, 7% SDS, 1 mM EDTA and 1% BSA for 16 hours and subsequently washing twice with 2×SSC and 0.1% SDS at 68° C.

Preferably the resistance gene coding for an autoactivated resistance protein originated from sugar beet or potato.

In a further preferred manner the inventive nucleic acid codes for an amino acid sequence with one of the consensus sequences according to SEQ ID NOS: 13 through 15. Within the consensus sequences functionally equivalent amino acids can be exchanged relative to each other, for example, Asp can be exchanged with Glu, Leu with Ile, Ala or Val, Arg with Lys, Phe with Trp.

The two consensus sequences according to SEQ ID NOS: 13 and 14 represent two functional blocks, of which the separation is not a fixed distance. A preferred separation between both blocks can be seen in the consensus sequence according to SEQ ID NO: 15 as well as in the consensus sequence according to FIG. 10.

The inventive nucleic acid is preferably combined with a pathogen inducible promoter. A pathogen inducible promoter is activated in reaction to the infection of the host tissue by a pathogen, for example a harmful fungi, a bacteria, a virus or a nematode. The pathogen inducible promoter is more active during the attempted or the successful infection of the plant tissue than in the non-infected plant tissue.

Pathogen inducible promoters are well known to the person of ordinary skill in this art. Examples of pathogen inducible promoters include a chitinase promoter (Samac and Shah 1991), a glucanase promoter (Henning et al., 1993) and the prp-1 promoter (Martini et al., 1993).

By the pathogen inducible overexpression of the R-gene, negative consequences of a constitutive expression, such as, for example, dwarfism or disfigurement of the plants, can be avoided.

Synthetic promoters have demonstrated themselves to be particularly suitable promoters. These include promoters produced by molecular biological techniques, which are not found in nature in this design. One such synthetic promoter is a minimalistic promoter, which besides a minimal promoter contains only one or more selected, defined cis-elements. These cis-elements are bonding sites for DNA-bonding proteins such as transcription factors and are isolated from natural promoters, derived from already isolated cis-elements or produced technically by chance oriented recombination techniques and are selected using suitable or appropriate processes. In comparison to a natural promoter, a synthetic promoter is only activated by few exogenous and endogenous factors due to its less complex construction and is thus regulated with more specificity.

The minimal promoter or "core" promoter is a nucleic acid sequence, which contains bonding sites for the basal transcription factor complex and enables the accurate initiation of transcription by the RNA-polymerase II. Characteristic sequence motifs of the minimal promoter are the TATA-box, the initiator element (Inr), the "TFBII recognition element" (BRE) and the "downstream core promoter element" (DPE). These elements can occur individually or in combinations in minimal promoters. The minimal promoter or its sequence motifs are obtainable from a generic plant or viral gene.

In the framework of the present invention new synthetic promoters have been developed, which even in connection with known resistance genes, which are not essential for coding for an autoactivated resistance protein, are usable for producing a pathogen resistant plant. These are promoters of type nxS-mxD-minimal promoters, nxW2-mxD-minimal promoters and nxGst1-mxD-minimal promoter, so that the synthetic promoter includes one or more of the following cis-element combinations:
  a) a nxS-mxD-Box
  b) a nxW2-mxD-Box
  c) a nxGst1-mxD-Box
(wherein n and m mean a natural number of 1 . . . 10)

The S-box (CAGCCACCAAAGAGGACCCAGAAT) with a nucleic acid sequence of SEQ ID NO: 6, the W2-box (TTATTCAGCCATCAAAAGTTGACCAATAAT) with nucleotide sequence SEQ ID NO: 7, the D-box (TACAAT-TCAAACATTGTTCAAACAAGGAACC) with nucleotide sequence SEQ ID NO: 8 and the Gst-box (TTCTAGCCAC-CAGATTTGACCAAAC) with the nucleotide sequence SEQ ID NO: 9 are described in Rushton et al., 2002 inclusive of the core sequences necessary for their functioning.

The promoters differentiate themselves in their base activity, pathogen inducibility, activation kinetics, and promoter strength respectively depending upon element selection (nxS-mxD, nxW2-mxD or nxGst1-mxD), as shown for example for promoters with the cis-element combinations 2xS-2xD with nucleotide sequence SEQ ID NO: 10, 2xW2-2xD with nucleotide sequence r SEQ ID NO: 11, and 2xGst1-2xD with nucleotide sequence SEQ ID NO: 12.

The characteristics of a synthetic promoter can be modified by changing the number of cis-elements (n, m=1 . . . 10) according to the requirements of the gene expression. The comparison of the promoter 2xS-2xD with the variants 2xS-4xD, 4xS-2xD and 4xS-4xD shows that the average promoter strength is increased by the use of tetramers in comparison to promoters constructed from dimers. Further, the pathogen inducibility increases from dimer-dimer promoter (2xS-2xD), beyond the tetramer-dimer and dimer-tetramer promoter (4xS-2xD, 4xS-2xD), to tetramer-tetramer promoter (4xS-4xD) at all measurement intervals. In parallel with the increase in promoter strength and pathogen inducibility, there results in the case of the described example also in an increase in the base activity of the tetramer containing promoters. This example shows that important promoter characteristics are also regulated by the number of the cis-elements and that for the respective technical translation or conversion optimal promoter variants can be produced and identified.

Suitable results can however also be obtained with cis-element combinations, which represent derivatives of the nucleotide sequence SEQ ID NO: 10, SEQ ID NO: 11 or SEQ ID NO: 12 and posses characteristics comparable to the cis-element combination of SEQ ID NO: 10, SEQ ID NO: 11 or SEQ ID NO: 12.

The promoters 2xS-2xD-minimal promoter and 2xW2-2xD-minimal promoter were combined, by way of exemplification, with the four full-length R-genes BvKWS3_133, BvKWS3_123, BvKWS3_135 and BvKWS3_165, and transformed in sugar beets. A fungal resistance test of the transgenic plants with the most important injurious fungus to the sugar beet, *Cercospora beticola*, the cause of leaf spot disease, resulted in each construct in an improved fungal resistance, while the transgenic plants did not differ in their growth or other agronomic characteristics from the non-transgenic plants. These results show that it is basically possible, with use of a pathogen inducible promoter, to achieve an overexpression of cell death triggering R-gene and therewith an improved disease resistance, without causing a negative influence on plant development. By use of optimized promoter following selection of the most suitable number of cis-element repetitions the disease resistance can be even further improved.

The present invention further concerns transgenic plants, which were transformed with the new nucleic acid construct, in particular sugar beet plants, part as well as seeds or genetic material of such plants, as well as use of the new nucleic acid construct for producing a transgenic plant.

The invention will be described in greater detail in the following with reference to the figures and examples.

The invention, described using sugar beets by way of example, can be easily translated to other agricultural plants from which resistance genes can be isolated.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10*a*)-*c*) show comparisons of the amino acid sequences of the shortened, autoactivated proteins Bv12069, Bv13033_#159, BvKWS135_#147, BvKWS3_165_#175 and StR3a-#1-155 with each other as well as with comparison sequences of nonactivated shortened resistance proteins from potato (RX-160) and StR1 (355-540) as well as complete R-proteins over the NBS-LRR type from *Arabidopsis thaliana* (AtAB028617), beans (PvulgarisJ71), rice (OsativaAP003073), soybean (GmaxKR4) and tomato (tomato-I2). Consensus sequences are highlighted.

DETAILED DESCRIPTION OF THE INVENTION

The invention as briefly described above is illustrated in greater detail in the following examples.

EXAMPLES

Verification of Initiation of Rapid Resistance Reaction in Sugar Beet Leaves by Overexpression of the Gene BvKWS3_133

Figure 1:
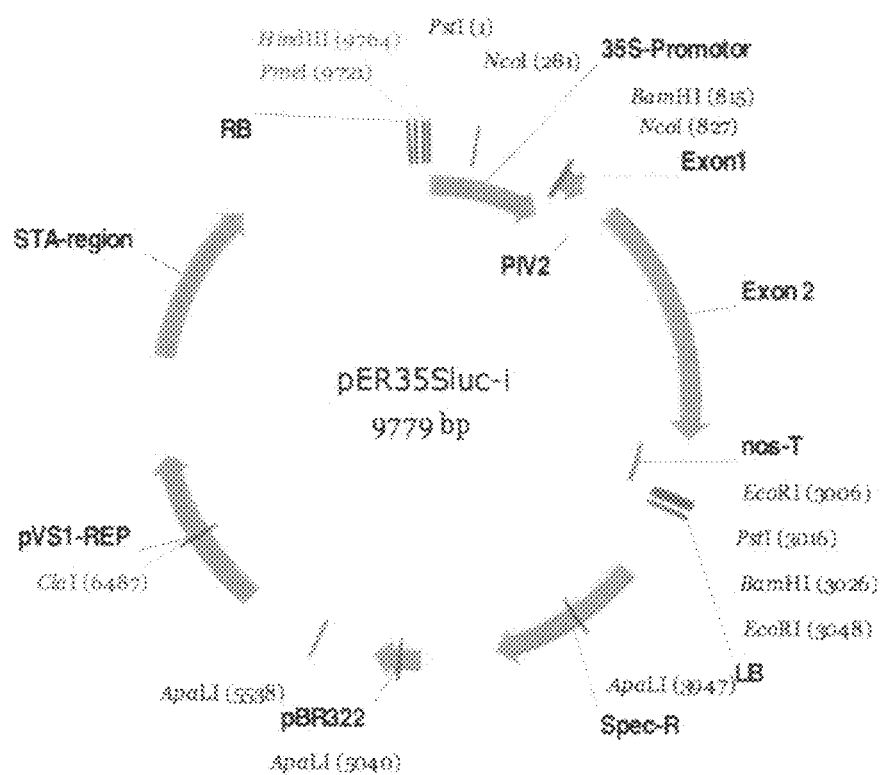
FIG. 1 shows the map of the binary vector pER-35Sluci, which was used for the *Agrobacterium tumefaciens* induced transient expression of R-genes in sugar beet leaves. The vector carries a luciferase gene from *Photinus pyralis* interrupted by an intron, which cannot be expressed in *A. tumefaciens*.
Figure 2:
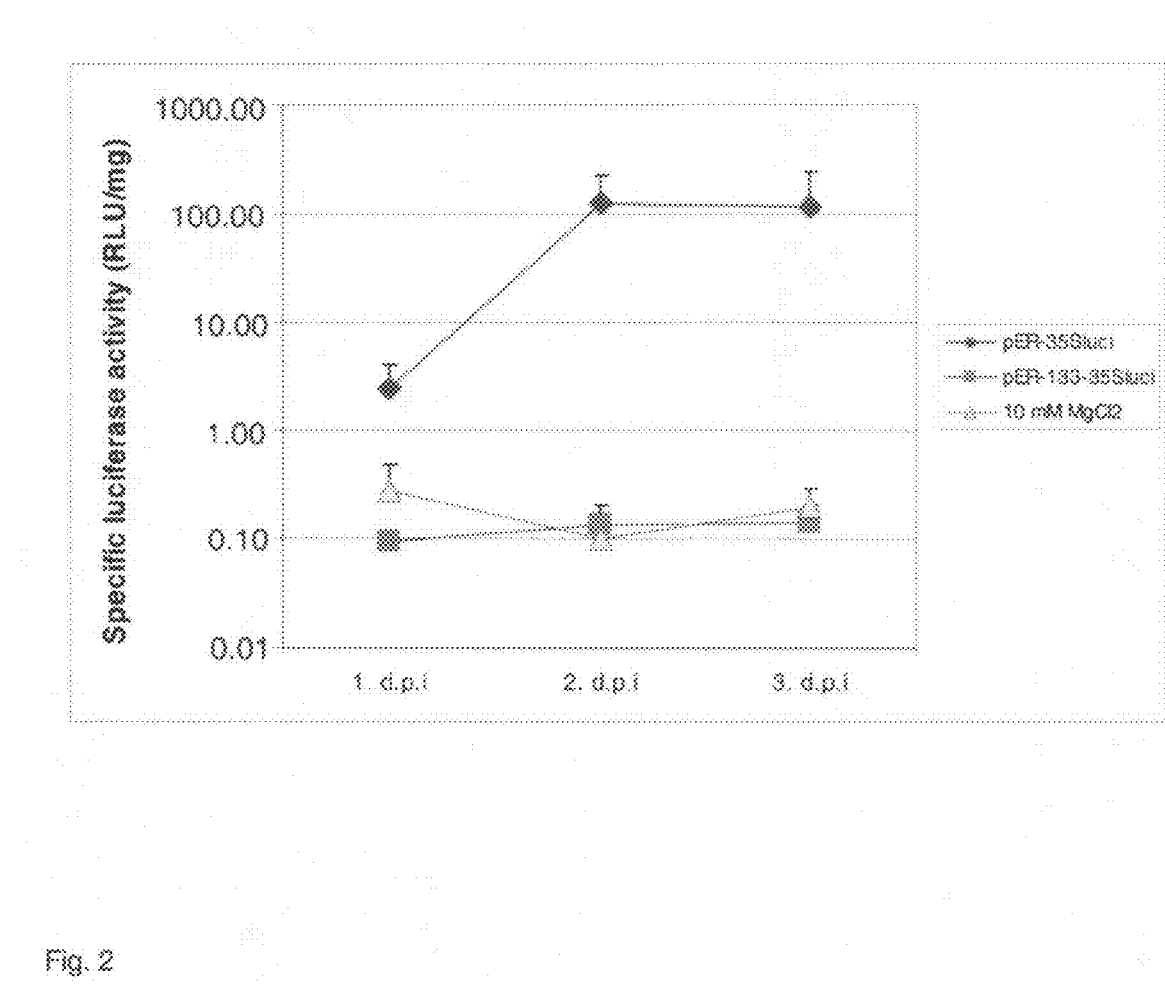
FIG. 2 shows the triggering of cell death in sugar beet leaves following transient expression of the R-gene BvKWS3_133 by *Agrobacterium tumefaciens*. While the transient expression of the construct pER-35Sluci leads to a strong reporter gene activity in beet leaves, the expression of the construct pER133-35Sluci triggers cell death so that no reporter gene activity can be measured.

The transient overexpression of the full-length cDNA clone of the gene BvKWS3_133 in sugar beet leaves by *Agrobacterium tumefaciens* triggers a rapid cell death without visible necrosis formation. The cDNA-clone BvkWS3_133 was combined with the d35S promoter and inserted in the binary vector pER-34Sluci (FIG. 1). The resulting vector was given the designation pER133-34Sluci. The vector pER-34Sluci and pER133-34Sluci were transformed in the *Agrobacterium* strain C58C1 (An 1987). Positive agrobacteria were cultured for the transient expression in 50 ml LB-medium with 100 mg/ml spectinomycin and 20 µM acetosyringon for 4-5 hours. Subsequently, the bacteria were centrifuged and the precipitate was taken up in a solution of 10 mM $MgCl_2$, 10 mM MES, 100 µM acetosyringon and adjusted to a bacteria density of $OD_{600}$=0.1. The bacteria suspension was allowed to rest for 2-3 hours and then injected into the leaves of old sugar beets with the aid of a 2.5 ml hypodermic needle via the underside of the leaf of 10 week old sugar beets. After incubation at 25° C. in an incubator, the *Photinus pyralis* luciferase reporter gene activity was measured in the transformed leaves in the 1, 2 and 3 days following inoculation. In addition, the luciferase activity was determined with the Luciferase Assay System (Promega, Mannheim, Germany) in a Sirius Luminometer (Berthold Detection System GmbH, Pforzheim, Germany) according to the manufacturer's specifications. For obtaining an enzyme suitable for the measurements, two leaf disks were stamped for each measurement interval. For each construct 8 measurement points were collected per measurement day. The leaf samples were homogenized in a mortise with addition of sea sand with the 10-fold volume (v/w) of Passive Lysis Buffer (PBL). The liquid supernatant was extracted and respectively 10 µl raw extract was employed for the *Photinus*-luciferase activity measurement. Sugar beet leaves which were transformed with the control construct pER-35Sluci, showed on day 1 a small and on 2 and 3 a luciferase activity of 124,000 or as the case may be 116,000 RLU/mg of leave tissue. Beet leaves, which were transformed with the construct pER-34Sluci, showed an activity at all three measurement points which was greater than the $MgCl_2$ inoculated leaves (FIG. 2). Thus, the transient expression of the cDNA clone BvKWS3__133 initiates a very rapid cell death in the inoculated beet leaves.

The Constitutive Expression of the R-Gene BvKW3__123, BvKWS3__133 and BvKWS3__165 Initiates a Cell Death in Sugar Beet Leaves.

Figure 3:
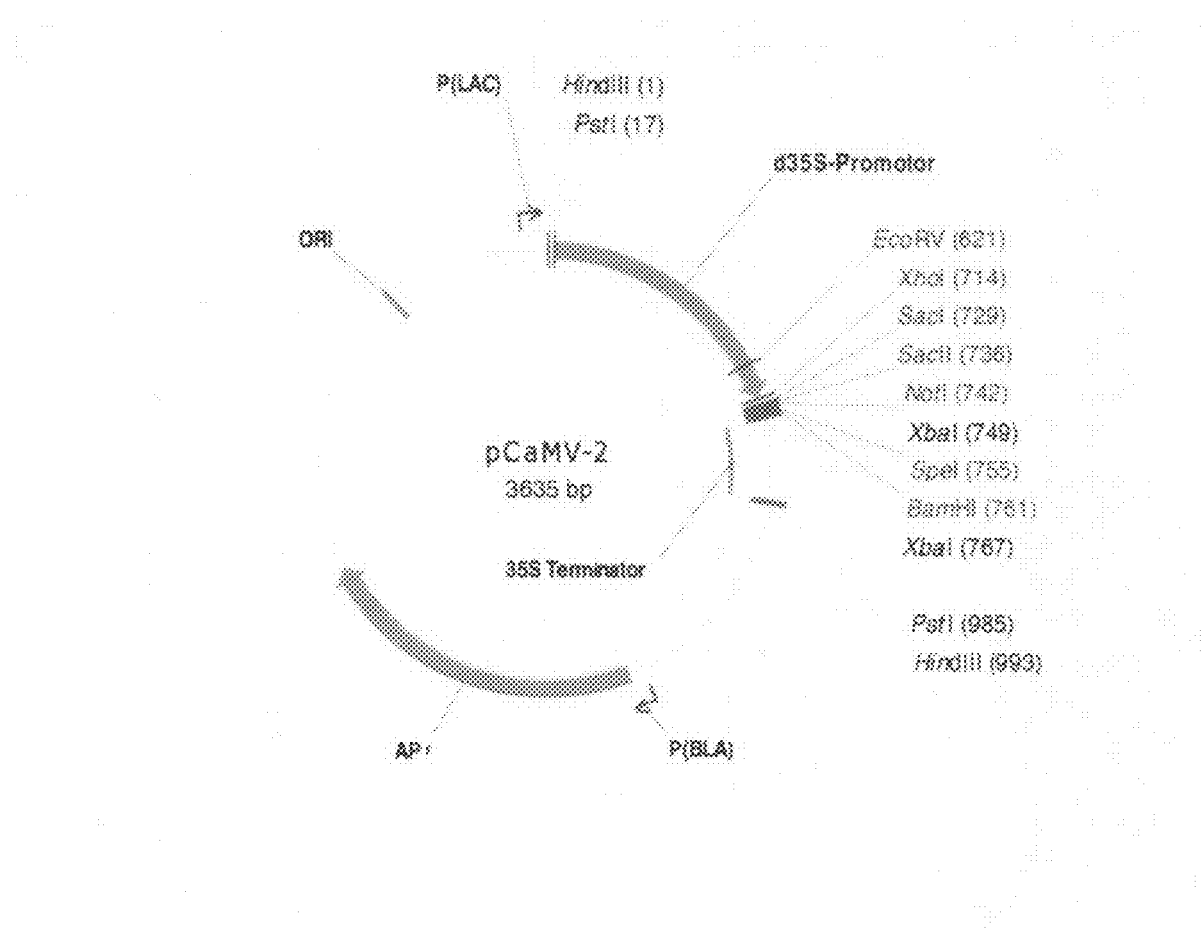
FIG. 3 shows the vector pCaMV-2 which was used for the transient, biolistic transformation of the sugar beet leaves. The full-length and shortened R-genes were placed under the control of the doubled 35 S promoter of this vector as described.
Figure 4:
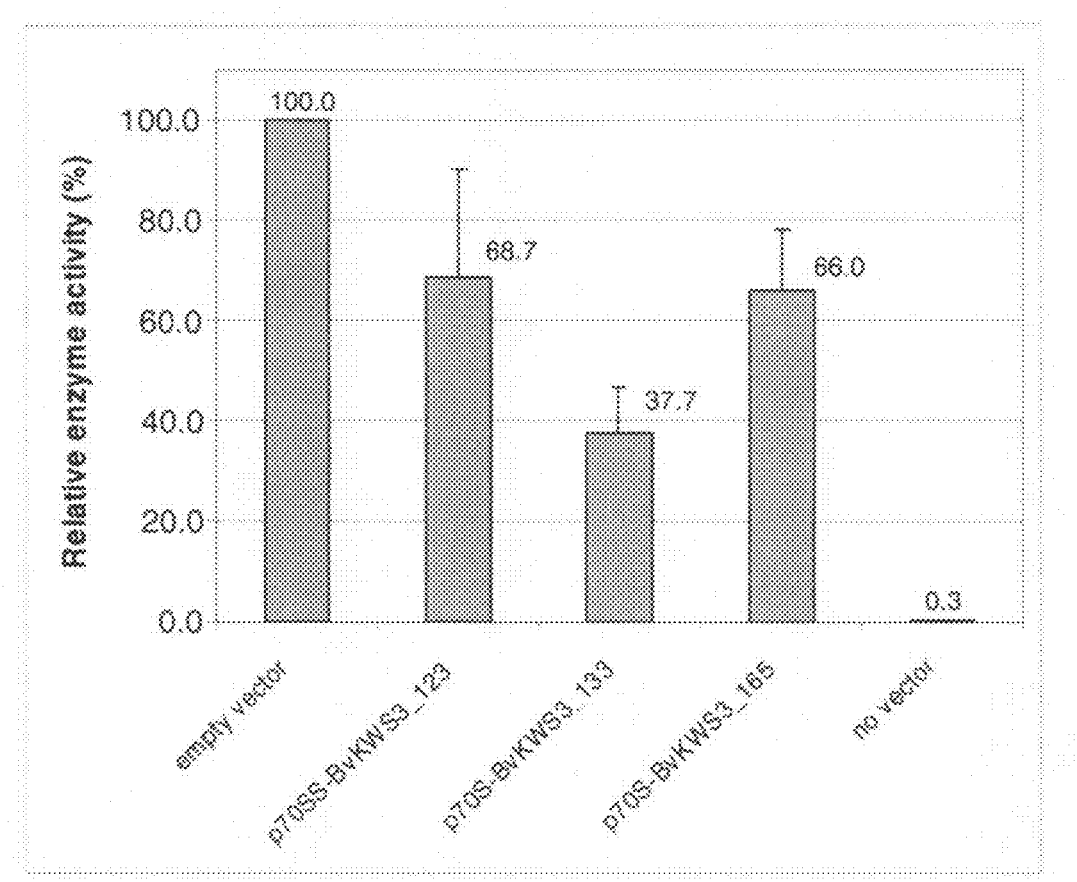
FIG. 4 shows the triggering of cell death in sugar beet leaves following transient expression of the R-gene BvKWS3_123, BvKWS3_133 and BvKWS3-165 by biolistic transformation. The genes BvKWS3_123, BvKWS3_133 and BvKWS3_165 are under the control of the doubled 35S-promoter (d35S) and were cotransformed with the reporter gene construct p70S-luc. The reporter gene activity was measured 20 hours following transformation. By triggering a hypersensitive reaction the reported gene activity is reduced in comparison to the control (Empty vector pCaMV-2 and p70S-luc). Shown is the average value of three independent test repetitions with respectively 9 individual experiments per construct. The error bar provides the standard error.

The R-gene BvKWS3__133 as well as the R-gene BvKWS3__165 with the nucleotide sequence according to SEQ ID No. 5 and the R-gene BvKWS3__123 were combined with the doubled 35S promoter of the vector pCaMV-2 (FIG. 3). The resulting vectors carry the designation p70S-BvkWS3__133, p70S-bvKWS3__165 and p70S-BvKWS3-123. In order to verify the functionality of the R-genes, the constructs p70S-BvkWS3__133, p70S-bvKWS3__165 and p70S-BvKWS3-123 were transiently expressed with the reporter gene vector p70S-luc in sugar beet leaves by biolistic transformation according to Schmidt et al. (2004). As a positive control, the empty vector pCaMV-2 was used in combination with the reporter gene vector P70S-luc. In contrast to Schmidt, et al. (2004), the use of a normalizing vector was dispensed with. The luciferase activity was determined with the Luciferase Assay System (Promega, Mannheim, Germany) 20 hours after the transformation. The transformation experiments were repeated three times, wherein each experiment included nine test repetitions per construct. The development of the average value from the three experiments showed that in comparison to the luciferase activity of the positive control (empty vector) set at 100%, the reporter gene activity for p70S-BvKWS3-133 only 37.7%, for p70S-BvKWS3__165 only 66% and for p70S-BvKWS3-123 only 68.7% (FIG. 4). The strong expression of the R-gene BVKWS3__133, BVKWS3__165 and BVKWS3__123 by the d35S promoter thus initiated cell death or as the case may be a hypersensitive reaction in one part of the transformed cells which prevented the co-expression of the simultaneously transformed reporter gene vector. Therewith it was shown that the strong expression of the three R-genes led to a cell death or, as the case a HR, in the absence of a corresponding avirulence gene product.

The 5' Area of the Gene BVKWS3__165 Triggers a More Rapid Cell Death than the Full-Length cDNA Clone BvKWS3__165

Figure 5:
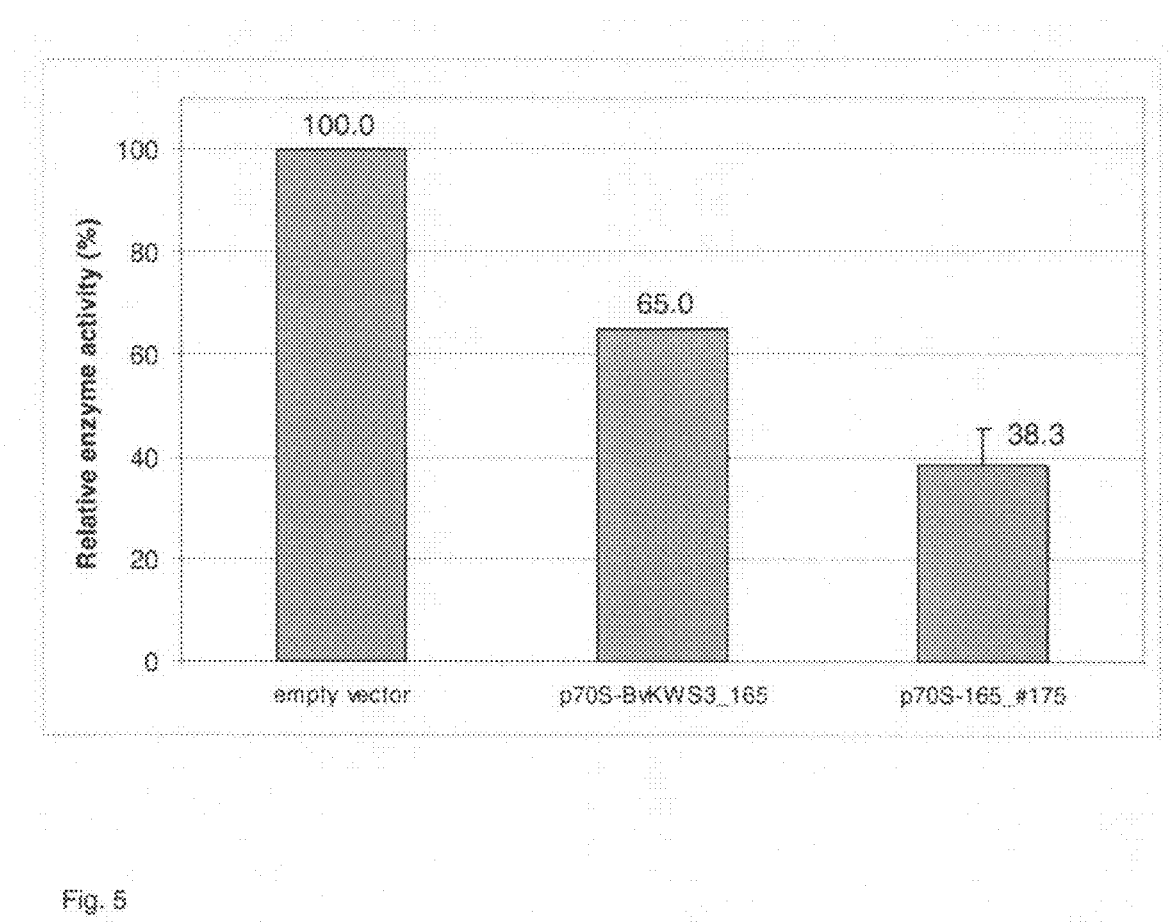
FIG. 5 shows an amplified cell death triggering by the expression by the 5'-terminal area of the R-gene BvKWS3_165 in comparison to the expression of the full-length R-gene BvKWS3_165. The N-terminal area and the full-length R-gene were cotransformed under the control of the d35S promoter (p70S-165_#175 and p70S-BvKWS3_165) with the construct p70S-luc by biolistic transformation in sugar beet leaves. Shown is the average of 3 independent test repetitions with respectively 9-12 individual experiments per construct.

Beginning with full-length cDNA clone BvKWS3.sub.__165 with the nucleotide sequence according to SEQ ID No. 5 in the construct p70S-BvKWS3.sub.__165, the 5' area of the gene was amplified with the aid of the Pfu-Polymerase (Stratagene) with use of the primer S316 (CTCGAGAATTC-GAGCTCCACCGCGG) with nucleotide sequence SEQ ID NO: 17 and S318 (CTGGATCCTCACCTCCGTTCTTCAT-GTTGCTCTACC) with nucleotide sequence SEQ ID NO: 18 and simultaneously a stop codon was introduced in the coded area. The amplified area corresponded to the nucleotide sequence according to SEQ ID No. 1 and encoded for the amino acid sequence 1-175 of BvKWS3.sub.__165 (FIG. 10). The amino acid sequence included only the N-terminal area of BvKWS3.sub.__165 and contained no NBS and no LRR domains (FIG. 10). The PCR product was cleaved with the restriction enzymes SacII and BamHI and cloned in the vector pCaMV-2. The resulting vector was given designation p70S-BvKWS3.sub.__#175. The ability of the construct P70S-BvKWS3.sub.__165 and p70-165.sub.__#175 to trigger a cell death in sugar beet leaves was tested quantitatively by transient biolistic transformation. For this, each vector was co-transformed with the reporter gene vector p70S-luc. As positive control the empty vector pCaMV-2 was used in combination with the reporter gene vector p-70S-luc. In comparison to transformation of the empty vector (pcAMV-2) the transformation of p70S-BvKWS3.sub.__165 resulted in 65% measurable reporter gene activity and the transformation of p70-165-#175 resulted in only 38% measurable reporter gene activity (FIG. 5). This result showed that the exclusive expression of the 175 amino acid sized N-terminus of 165.sub.__#175 led to an intensive triggered of cell death in the transformed sugar beet leaves than the use of the 1066 amino acid sized full-length protein BvKWS3.sub.__165. By expression of 165.sub.__#175 more of the transformed leaf cells die off than in the case of the expression of BvKWS3.sub.__165. The cause for this difference is a new, more intensive form of the autoactivation of the R-protein by the shortening (contraction) at the N-terminus.

The 5'-Area of the Gene BvKWS3__135 Triggers a More Rapid Cell Death than the Full-Length cDNA Clone BvKWS3__135

Figure 6:
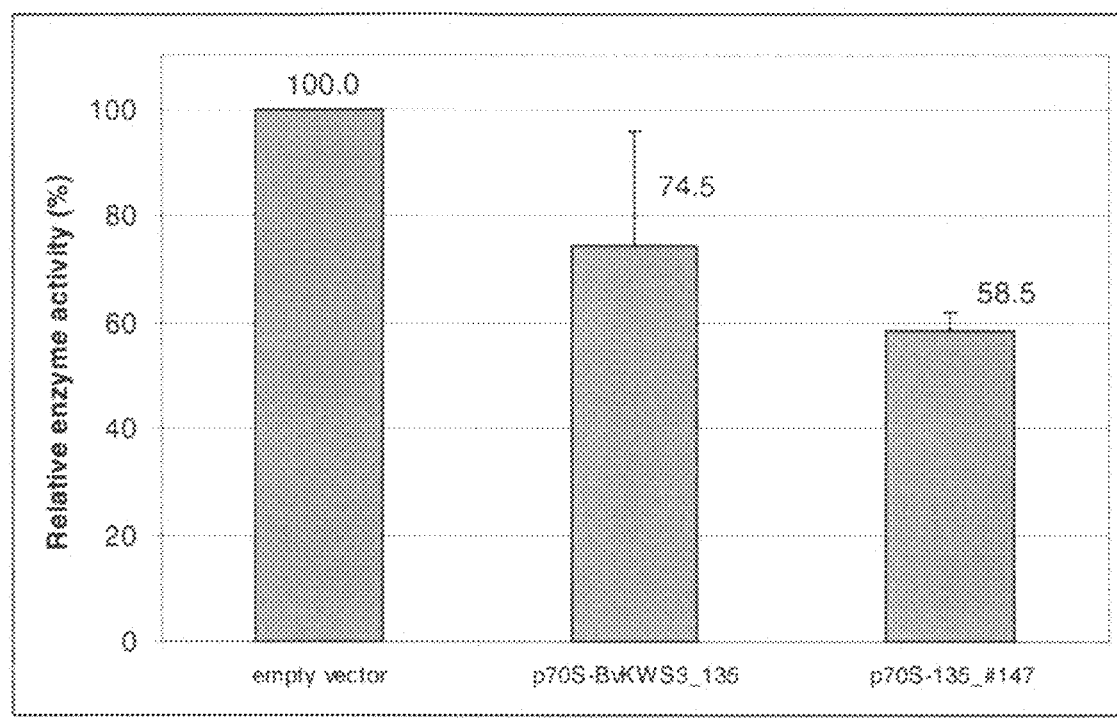
FIG. 6 shows cell death triggering by the expression of full-length R-gene BvKWS3_135 in comparison to the amplified cell death triggered by the 5'-terminal area 135_#147 of the R-gene BvKWS3_135. The full-length R-gene and the N-terminal area 135_#147 were cotransformed under the control of the d35S promoter (p70S-BvKWS3_135 and p70S-135_#147) with the construct p70S-luc by biolistic transformation in sugar beet leaves. Shown is the average of 2 independent test repetitions with respectively 9-12 individual experiments per construct.

Beginning with full-length cDNA clone BvKWS3.sub.__135 in the construct p70S-BvKWS3.sub.__135 the 5'-area of the gene was amplified with the aid of the Pfu-polymerase (Stratgene) with use of the primer S316 (CTCGAGAATTC-GAGCTCCACCGCGG) (SEQ ID NO: 17) and S330 (CTG-GATCCTCAGGGAGAACTCCATCTGGGTGGTCC) with nucleotide sequence SEQ ID NO: 19 and simultaneously a stop codon was introduced in the coded area. The amplified area corresponds to the nucleotide sequence according to SEQ ID NO. 2 and codes for the amino acid sequence 1-147 of BvKWS3.sub.__135 (FIG. 10). The amino acid sequence includes only the N-terminal area of BvKWS3.sub.__135 and contains no NBS and no LRR domains or, as the case may be, motifs from these domains. The PCR product was cleaved with the restriction enzymes SacII and BamHI and cloned in the vector pCaMV-2. The resulting vector was given the designation p70S-135.sub.__#147. The ability of the construct p70S-BvKWS3.sub.__135 and p70S-135.sub.__#147 to trigger a cell death in sugar beet leaves was tested quantitatively by transient biolistic transformations. For this, each vector was co-transformed with the reporter gene vector p70S-luc. As positive control the empty vector pCaMV-2 was used in combination with the reporter gene vector p70S-luc. In comparison to transformation of the empty vector (pCaMV-2), the transformation of p70S-BvKWs3.sub.__135 led to 74.5% measurable reporter gene activity and the transformation of p70s-135.sub.__#147 led to only 58% measurable reporter gene activity (FIG. 6). The result showed that the expression of the full-length clone BvKWS3.sub.__135 led to triggering of cell death in the transformed tissue. However, the exclusive expression of the 147 amino acid sized N-terminus of 135.sub.__#147 brought about a more intensive cell death in the transformed sugar beet leaves than the use of the 844 amino acid sized protein BvKWS3.sub.__135. By expression of 135.sub.__#147 more transformed leaf cells died than in the case of the expression of BvKWS3.sub.__135. The cause of this difference is a new, more intensive form of the autoactivation of the R-protein by the contraction or shortening at the N-terminus The 5'-Area of the Gene Bv13033 Triggers a More Rapid Cell Death than the Full-Length cDNA Clone Bv13033

Figure 7:
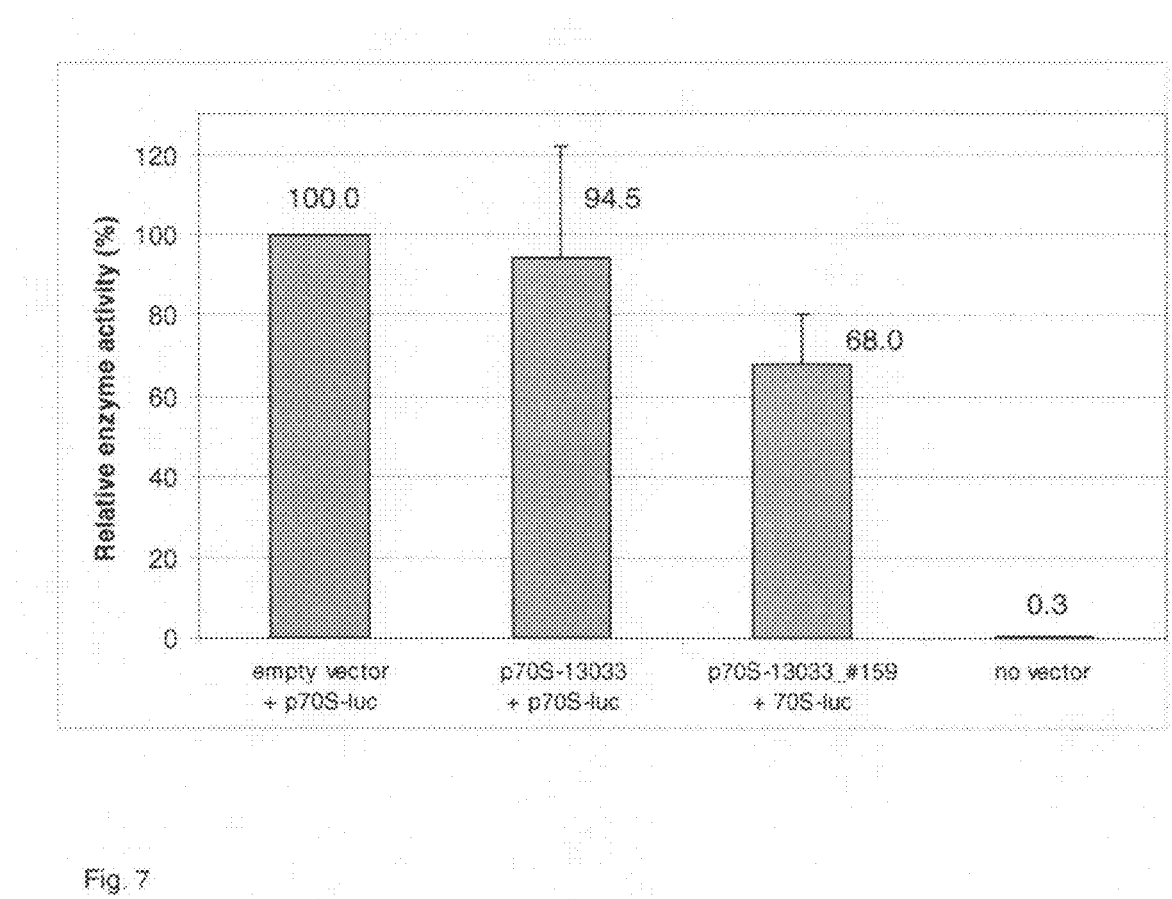
FIG. 7 shows an amplified cell death triggering by the expression of the 5'-terminal area 13033_#159 of the R-gene Bv13033 in comparison to the expression of the full-length R-gene Bv13033. The full-length R-gene and the N-terminal area 13033_#159 were cotransformed under the control of the d35S promoter (p70S-13033 and p70S-13033_#159) with the construct p70S-luc by biolistic transformation in sugar beet leaves. Shown is the average of 2 independent test repetitions with respectively 9-12 individual experiments per construct.

Beginning with full-length cDNA clone Bv13033 in the construct p70S-Bv13033 the 5'-area of the gene was amplified with the aid of the Pfu-polymerase (Stratagene) with use of the primer S316 (CTCGAGAATTCGAGCTCCAC-CGCGG) (SEQ ID NO: 17) and S333 (CTGGATCCTCAA-GAACAAGTCTCAGGCCTTCTGTT) with nucleotide sequence SEQ ID NO: 20 and simultaneously a stop codon was introduced in the coded area. The amplified area corresponds to the nucleotide sequence according to SEQ ID No: 3 and codes for the amino acid sequence 1-159 of Bv13033 (FIG. 10). The amino acid sequence includes only the N-terminus area of Bv13033 and contains no NBS and no LRR domains or motifs from these domains. The PCR product was cleaved with the restriction enzymes SacII and BamHI and cloned in the vector pCaMV-2. The resulting vector was given the designation p70S-13033.sub.__#159. The ability of the construct p70s-13033 and p70s-13033.sub.__#159 to trigger a cell death in sugar beet leaves was tested quantitatively by transient biolistic transformations. For this, each vector was co-transformed with the reporter gene vector p705-luc. As positive control the empty vector pCaMV-2 was used. In comparison to transformation of the empty vector (pCaMV-2), the transformation of p70s-13033 led to 95% measurable reporter gene activity and the transformation of p70s-165.sub.__#175 led to only 68% measurable reporter gene activity (FIG. 7). The results showed that the expression of the full-length clone Bv13033 led to the triggering of only a weak cell death in the transformed tissue. The exclusive expression of the 159 amino acid sized N-terminus of 13033.sub.__#159 brought about on the other hand an intensive cell death in the transformed sugar beet leaves. The cause of this difference is a new, more intensive form of the auto-activation of the R-protein by the shortening at the N-terminus.

Triggering of Cell Death in Sugar Beet Leaves by the 5'-Area of the Gene Bv12069

Figure 8:
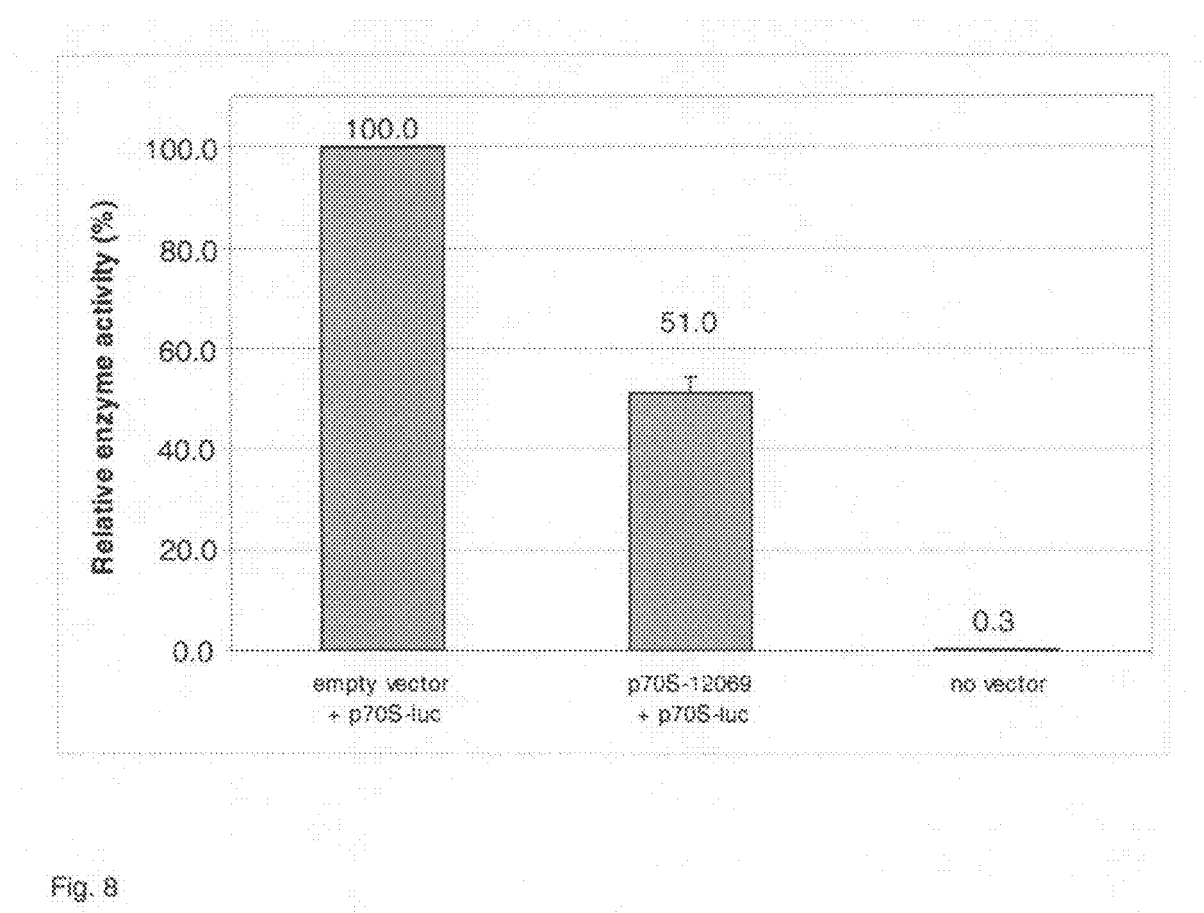
FIG. 8 shows the initiation of cell death by the expression of R-gene Bv12069.

The R-gene Bv12069 with the nucleotide sequence according to SEQ ID No. 4 codes for the 166 amino acid sized N-terminus of R-protein. The protein Bv12069 contains no NBS and no LRR domains, however, evidences a distinct homology to the 175, 147 and 159 amino acid sized N-termini of the autoactivated R-proteins 165__#175, 135__#147, 13033__#159 (FIG. 10). The cDNA clone was combined with doubled 35S promoter of vector pCaMV-2 (FIG. 3) to form the vector p70S-12069. In order to check the functionality of the gene Bv12069, the construct p70S-12069 was expressed in combination with the reporter gene vector p70S-luc in sugar beet leaves transiently by biolistic transformation. The reporter gene activity in the leaves transformed with p70S-12069 and p70S-luc amounted in three independent tests to 51% of the activity which could be measured in the positive control (empty vector pCaMV-2 and p70S-luc) (FIG. 8). The expression of the 166 amino acid sized protein Bv12069 therewith triggered a cell death in sugar beet cells.

Figure 9:
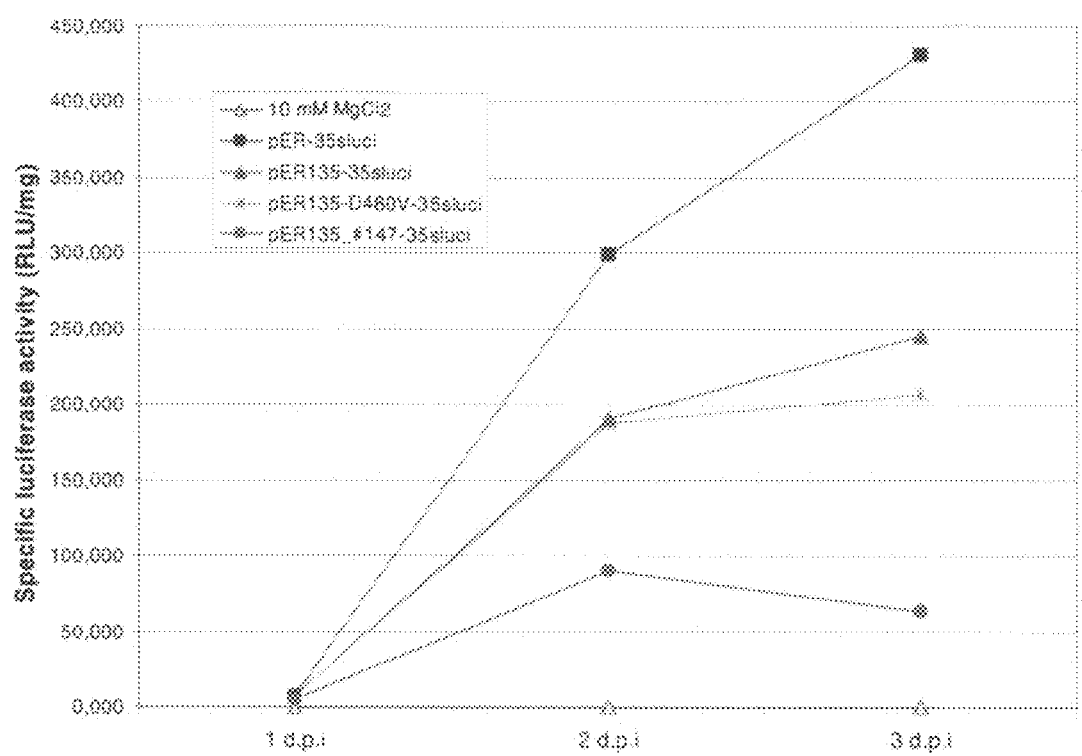
FIG. 9 shows the autoactivation of the protein BvKWS3_135 by shortening at the 5' area of the cDNA clone 135_#147 in comparison to the mutation of the VHD Motif of the NBS Domain.

The Shortening of the Gene BvKWS3__135 Results in an Autoactivated R-Protein, However not the Mutagenesis of the MHD Domains The inventive mechanism of the autoactivation by condensation of a R-protein of the NBS-LRR type to the NBS- and LRR free N-terminus was compared with the method of autoactivation by mutagenesis of the MHD motif. The mutagenesis of the MHD motif of the Rx-gene of the potato and the L5 gene of flax led to an autoactivation of the indicated gene (Bendahamane et al., 2002; Howes et al., 2005). The cDNA clone BvKWS3__135 does for the MHD motif equivalent to the VHD motif, a motif that besides the MHD motif is likewise frequently found is R-gene (Howles et al., 2005). The corresponding mutation was, as described in Bendahmane et al. (2002), introduced in the full-length clone BvKWS3__135. For this, the amino acid aspartate in the VHD motif of the gene BvKWS33__135 was exchanged with the amino acid valine. The resulting gene was given designation BVKW3__135_D480V. The effectiveness of the gene 135__#147, BvKWS3__135-D408V and the non-modified gene BvKWS3__135 were tested by *Agrobacterium tumefaciens* initiated transient overexpression in sugar beet leaves. For this the cDNA clone BvKWS3__135 was combined with the d35S promoter and inserted in the binary vector pER-34Sluci. The resulting vector was given the designation pER135-34Sluci. Similarly there were processed the shortened cDNA clone 135__#147 with a nucleotide sequence according to SEQ ID No. 2 as well as with the mutantgenized cDNA clone BvKWS3__135_D408V. The resulting vectors were given designation pER135__#147-35Sluci and pER135_D480V-35Sluci. The vectors were transformed in *Agrobacterium* of strain or line C58C1 as described and injected in sugar beet leaves simultaneously with the control pER-35Sluci. The *Photinus pyralis* luciferase-reporter gene activity was measured 1, 2 and 3 days post inoculation in the transformed leaves. Sugar beet leaves, which were transformed with the control construct pER-35Sluci showed on day 1 a small and the $2^{nd}$ and $3^{rd}$ day a luciferase activity of 299,000 and 433,000 RLU/mg leaf tissue. Beet leaves which were transformed with the construct pER135-35Sluci showed on day 2 and day 3 a luciferase activity of 190,000 and 245,000 RLU/mg leaf tissue and therewith, in comparison to the positive control pER-35Sluci, a measurable cell death. The reported gene activity of the construct pER__135_D480V-35Sluci amounted on day 2 and day 3 to 188,000 and 206,000 RLU/mg (FIG. 9). Accordingly the introduction of the MHD mutation in the gene BvKWS3__135 resulted in no, or a barely measurable, autoactivation. The R-gene 135__#147 shortened in accordance with this process showed on day 2 and 3 a reporter gene activity of 90,000 and 63,000 RLU/mg (FIG. 9) and therewith a significantly stronger cell death initiation and autoactivation than the construct pER135-35Sluci and pER__135_D480V-35Sluci.

Identification of Common Amino Acid Motifs in the N-Termini of the R-Protein of BvKWS3__165, BvKWS3__135. Bv13033 and Bv12069 und StR3a A homology comparison between the 175, 147, 159 und 166 amino acid sized N-terminus of the R-proteins BvKWS3__165, BvKWS3__135, Bv13033 and Bv12069 and the 155 amino acid sized N-terminus of the R3a gene of the potato (Huang et el., 2005) was carried out in order to identify common sequence motifs. The comparison lead to the identification of multiple consensus sequences in the N-termini of the autoactivated R-protein. The common sequence motifs are highlighted as consensus sequences in FIG. 10a).

One consensus sequence corresponds to the amino acid sequence according to SEQ ID NO: 13: AVLXDAEXKQXX XXXLXXWLXD LKDXVYDXDD ILDE. Another consensus sequence corresponds to the amino acid sequence according to SEQ ID NO: 14: IXEIXXKLDD L The letter X refers herein to any amino acid.

Figure 10B:
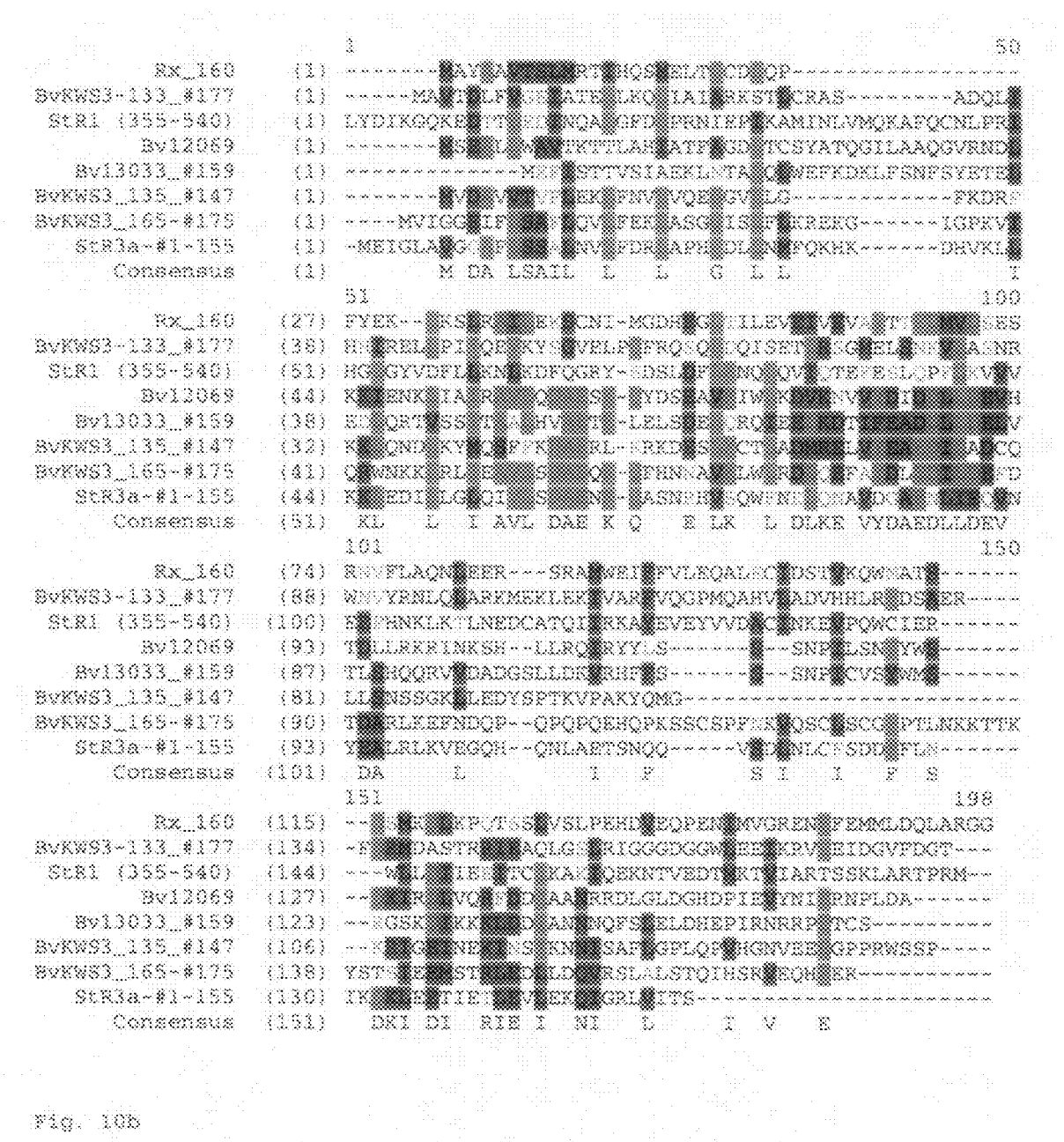
Figure 10C:
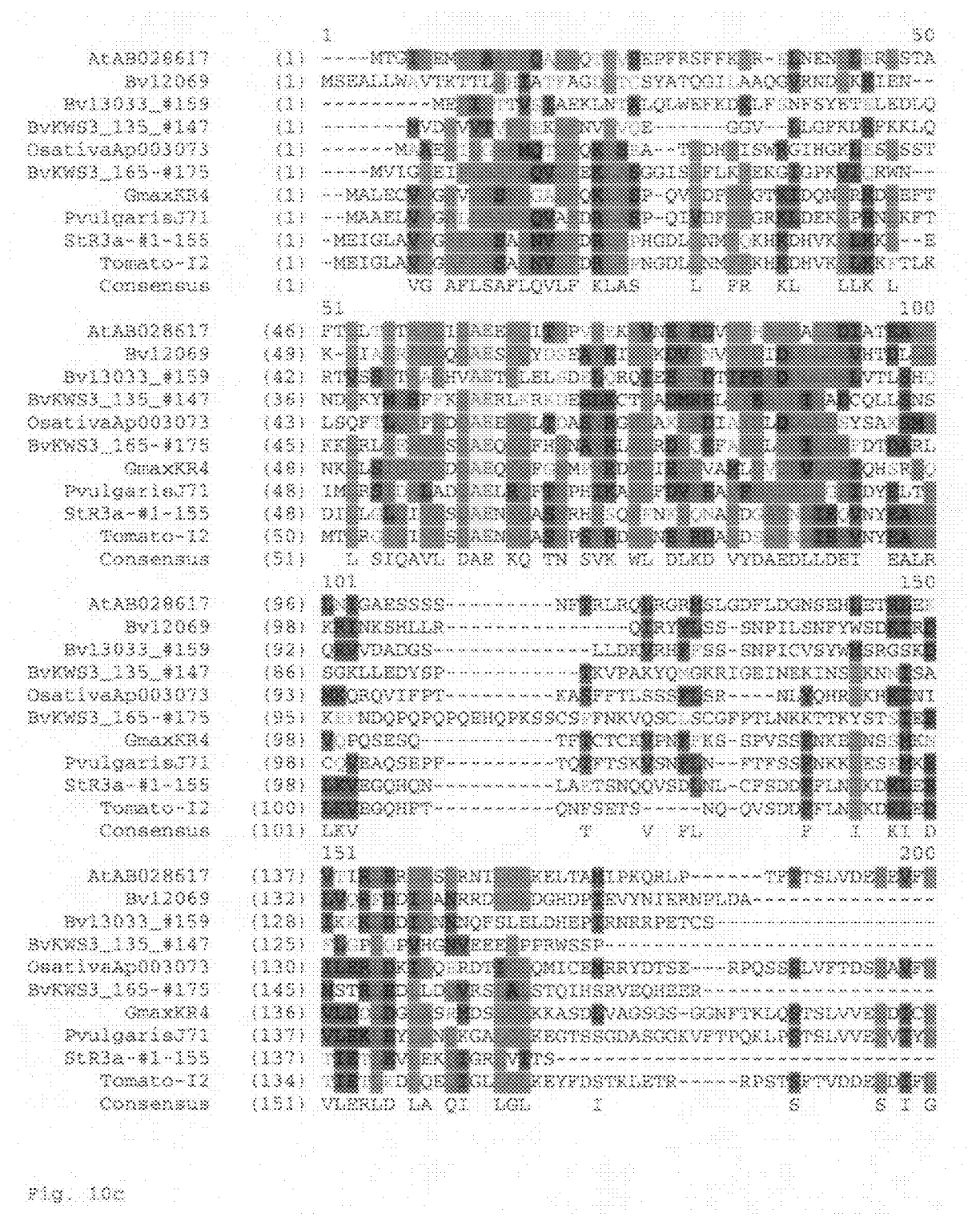

Both consensus sequences in the described form are contained only in such N-termini of CC-NBS-LRR R-proteins in which the expression leads to an autoactivation. Thus, the 160 amino acid sized CC-domain of the RX-gene is not capable of initiating cell death or, as the case may be, a hypersensitive reaction (Bendahmane et al., 2002). The transient expression of the 177 amino acid sized N-terminus of the R-gene BvKWS3_133_e08 of sugar beet and the 540 amino acid sized N-terminus of the R1 gene of the potato (Ballvora et al., 2002) initiated in comparison to the full-length R-gene BvKWS3_133_e08 no amplified or, in the case of the R1 gene, no cell death (data not shown). The amino acid comparison of the N-termini of the autoactivated proteins BvKWS3_165_#176, BvKWS3_135_#147, Bv13033_#159, Bv12069 und StR3a-#1-155 with the amino acid sequences of the CC-domain of the Rx-, StR1-und BvKWS3_133_#177-protein show the absence of the above described consensus sequences in the not autoactivated N-termini (FIG. 10b). In particular the sequence motif DAE is an important aid of identification of R-proteins, of which the N-terminus is autoactive. With the aid of the sequence motif DAE in the consensus sequence suitable R-genes for an autoactivation can be found in numerous plant species, as shown in FIG. 10c for examples of *Arabidopsis thaliana* (AtAB028617), bean (PvulgarisJ71), rice (osativaAp003073), soy bean (GmaxKR4) und tomato (Tomato-I2).

The Amino Acid Sequence of 147-175 is Important for the Autoactivation of the R-Protein 165_#175

Figure 11:
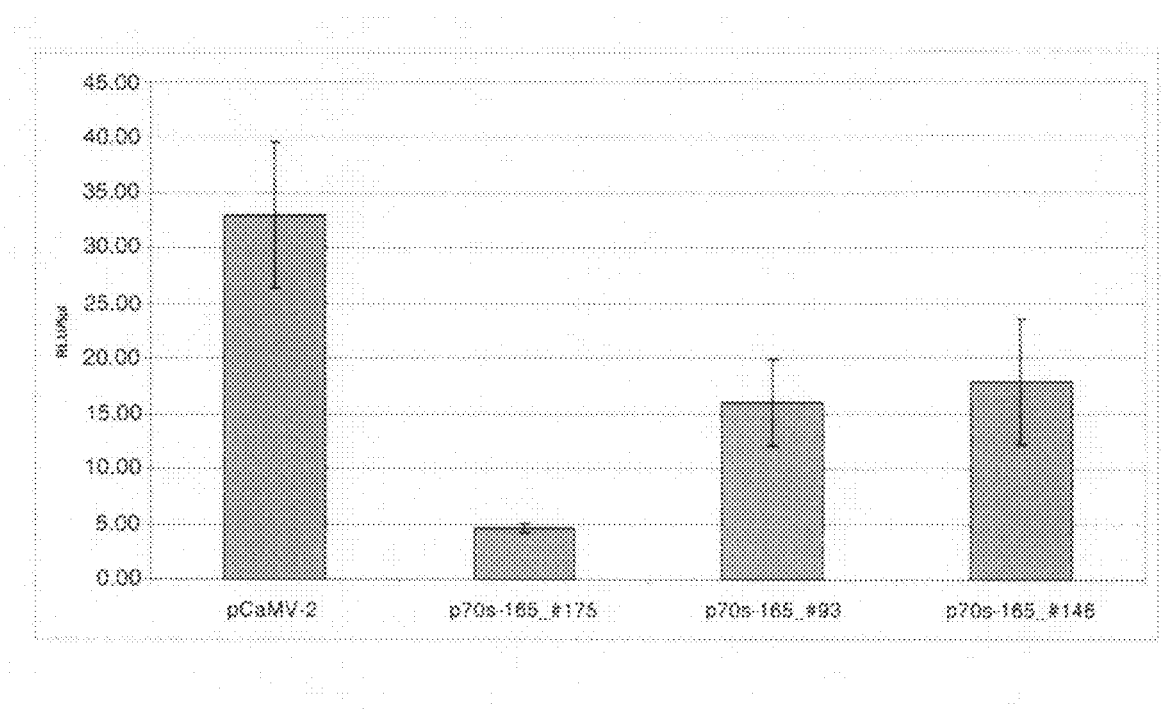
FIG. 11 shows that the deletion of the amino acids 147-175 significantly reduces the autoactivatability of the proteins 165_#175.

In order to identify the amino acid section in the protein 165_#175 which is important for the autoactivation of the N-terminus of NBS-LRR proteins, the encoding region of the cDNA clone 165_#175 was shortened. The cDNA clones 165_#93 and 165_#146 coded for the amino acid 1-93 or as the case may be 1-146 of the protein 165_#175. The transient biolistic test of the constructs p70S_165_#93, p70S_165_#146 and p70S_165_#175 showed that only the protein 165_#175, however not 165_#93 and 165_#146, triggered a strong cell death (FIG. 11). Accordingly the sequence region of 146-175 is essential for the autoactivation of NBS-LRR proteins. In this region there lies a sequence motif conserved in all examined proteins (FIG. 10a).

Rapid Activation of the Synthetic Pathogen Inducible Promoters 2xS-2xD and 2xW2-2xD by Fungal Infestation For the pathogen induced overexpression of complete or partial resistance genes, particularly suited are synthetic promoters of type nxS-mxD, nxW2-mxD and nxGst1-mxD, wherein n=1, 2, 3, 4, 5, 6, 7, 8, 9, 10 and m=1, 2, 3, 4, 5, 6, 7, 8, 9, 10. For example, promoters of type 2xS-2xD according to SEQ ID NO. 10, 2xW2-2xD according to SEQ ID NO. 11 as well as 2xGst1-2xD according to SEQ ID NO. 12 were combined with the luciferase gene from *Photinus pyralis*, transformed in sugar beets and analyzed in reaction to fungal infestation.

For the plant transformation the binary vectors 2xS-2xD-luc-kan, 2xW2-2xD-luc-kan, and 2xGst1-2xD-luc-kan were found to be useful. The binary vectors were transformed in the *Agrobacterium tumefaciens* type C58C1 with the resident plasmid pGV2260 by a direct DNA-transformation process (An, 1987). The selection of recombinant *A. tumefaciens* clones occurred using the antibiotic kanamycin (50 mg/l).

The transformation of the sugar beets occurred according to Lindsey et al. (1991) using the antibiotic kanamycin. The transgenecity of the plants was tested by PCR. The use of the primer GTGGAGAGGCTATTCGGTA and CCACCATGATATTCGGCAAG lead to the amplification of the 553 base pair sized DNA-fragment from the nptII-gene. The PCR was carried out using 10 ng genomic DNA, a primer concentration of 0.2 µM at an annealing temperature of 55° C. in a Mutli-Cycler PTC-200 (MJ Reasearch, Watertown, USA).

In order to analyze the pathogen inducibility of the promoter, the transgenic sugar beets were infected under in-vitro conditions with a leaf spot inducer of sugar beets, *Cercospora beticola*. Respectively 4 plants of a transgenic line dipped in a suspension of *C. beticola* mycelium fragments (400,000 fragment/ml) and 4 plants were dipped for control purposes in dilute vegetable juice. Infected plants and control plants were subsequently incubated at 25° C. and 16 h illumination in a culture cabinet. Infected and non-infected leaf material was removed 1, 2, 3, 4 and 6-7 days subsequent to the inoculation and the luciferase reporter gene activity was determined with the Luciferase Assay System (Promega, Mannheim, Germany) as described.

Figure 12:
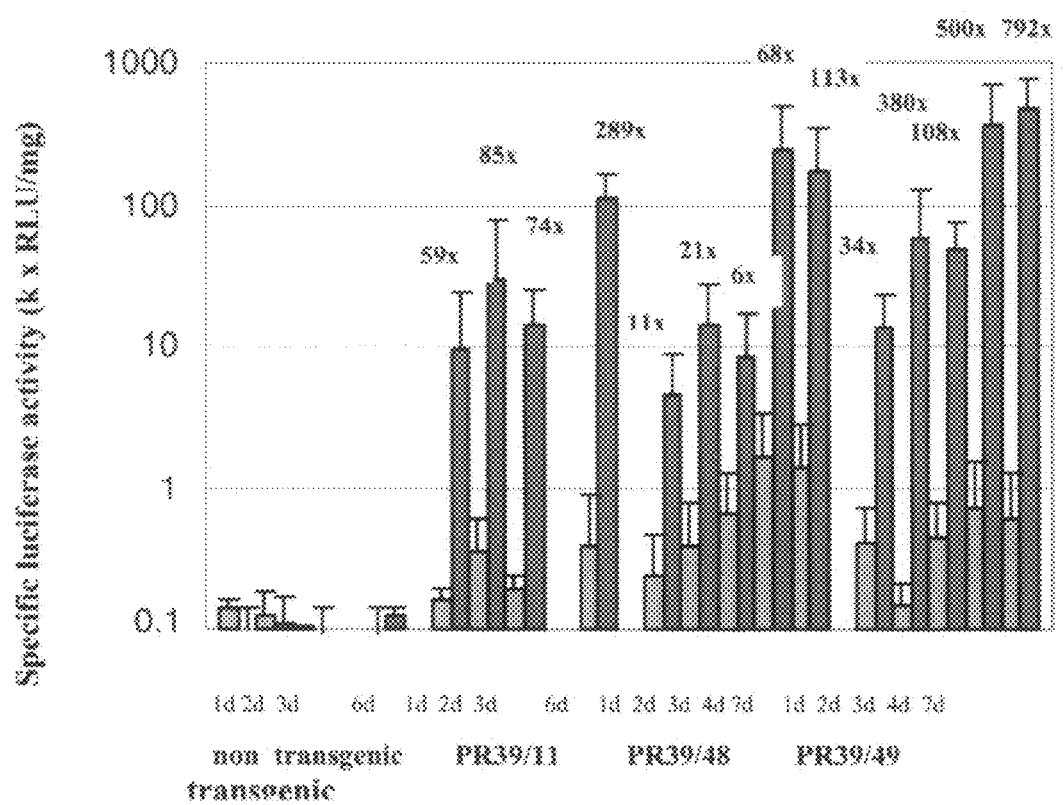
FIG. 12 shows the activation of the synthetic promoter 2xS-2xD in transgenic sugar beets following *cercospora beticola* infestation.
Figure 13:
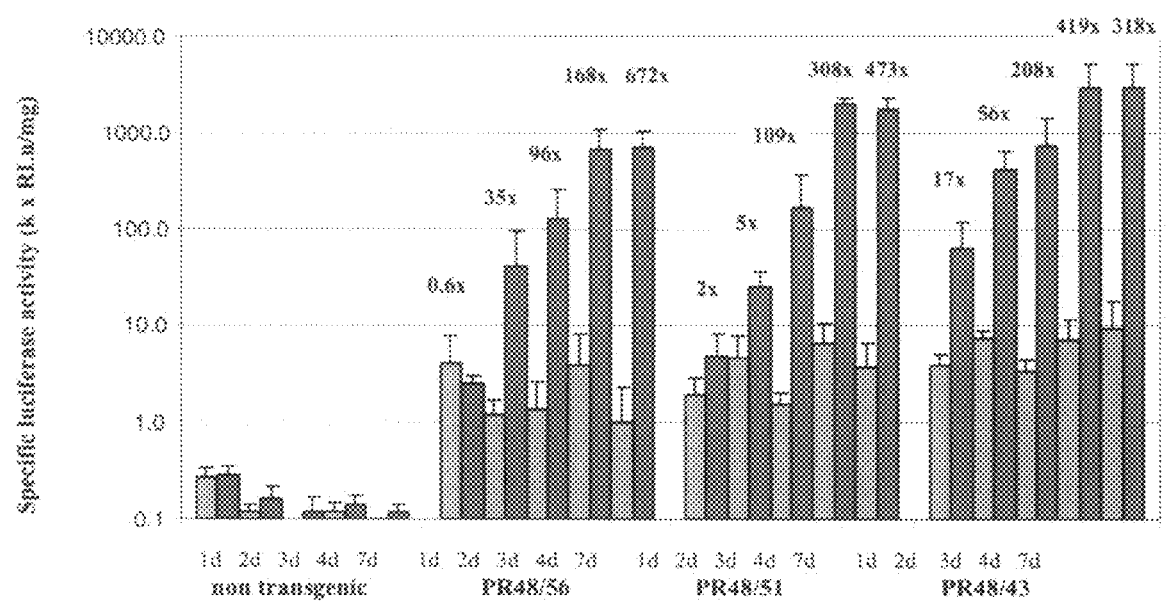
FIG. 13 shows the activation of the synthetic promoter 2xW2-2xD in transgenic sugar beets following *cercospora beticola* infestation.

Both the 2xS-2xD as well as the 2xW2-2xD promoter showed a rapid and strong pathogen inducibility in the early phase of the infection, differed however in base activity and promoter strength (FIG. 12-13). The 2xS-2xD-promotor was rapidly induced in the case of the transgenic lines PR39/11, PR39/48 and PR39/49, already 11-59 fold on the first day after inoculation and 21-384 fold on the second day in comparison to the non-infected plants (FIG. 12). While day 1 is still characterized by a growth of the fungal hyphae on the epidermis, on day 2 there is a penetration of the leaves through the stomata and therewith a penetration into the leaf tissue. In the late phase of the infection at day 7, a 113-792 fold induction of the promoter was measured with a visible development of the necrosis. The base activity of the 2xS-2xD promoter measured as reported gene activity of the non-infected plats is very small and amounted to only the 1-10 fold of the luciferase activity measurable in the non-transgenic plants.

The activation of the 2xW2-2xD promoter progressed somewhat slower than that of the 2xS-2xD promoter. On the first infection day the 2xW2-2xD promoter exhibited only a 2-11 fold, and on the second infection day a 5-56 fold, pathogen induction. With the occurrence of the necrosis on day 7, a maximal 318-672 fold pathogen induction was achieved (FIG. 13). The base activity of the 2xW2-2-D promoter, having a 10-50 fold of reporter gene activity measurable in comparison to the non-transgenic plants, is higher than in the case of the 2xS-2xD promoter. Significantly the 2xW2-2xD promoter exceeds the 2xS-2xD promoter by its approximately 10-fold higher promoter strength.

Optimization of the Promoter Characteristics by Changing the cis-Element-Number.

The characteristic of a synthetic promoter of type nxS-mxD, nxW2-mxD and nxGst1-mxD with n=1, 2, 3, 4, 5, 6, 7, 8, 9, 10 and m=1, 2, 3, 4, 5, 6, 7, 8, 9, 10 can be modulated and optimized by variation of the number of the cis-elements according to the requirements of the gene expression. This is shown for illustrative purposes for the promoter type nxS-mxD. Besides the binary vector 2xS-2xD-luc-kan the binary vectors 4xS-2xD-luc-kan, 2xS-4xD-luc-kan and 4xS-4xD-luc-kan were constructed and transformed in sugar beets. The transgenic plants were infected with *C. beticola* as described and reporter gene activity was measured daily subsequent to fungal inoculation. The test results from 13 independent 2xS-2xD-luc lines, 14 independant 4xS-2xD-luc lines, 15 independent 2xS-4xD-luc lines as well as 15 independent 4xS- 4xD-luc lines were determined and the measurement values were compared in their promoter strength, pathogen induction and base activity.

Figure 14:
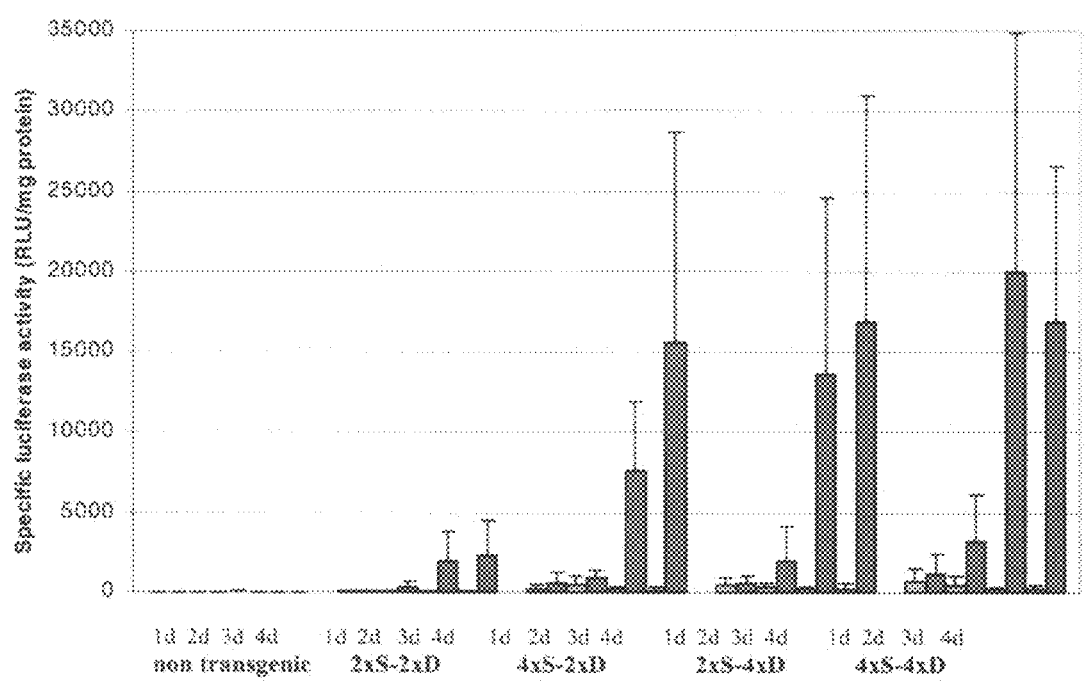
FIG. 14 shows the comparison of the reporter gene activity of promoters 2xS-2xD, 4xS-2xD, 2xS-4xD and 4xS-4xD in transgenic sugar beets following *Cercospora beticola* infestation.
Figure 15:
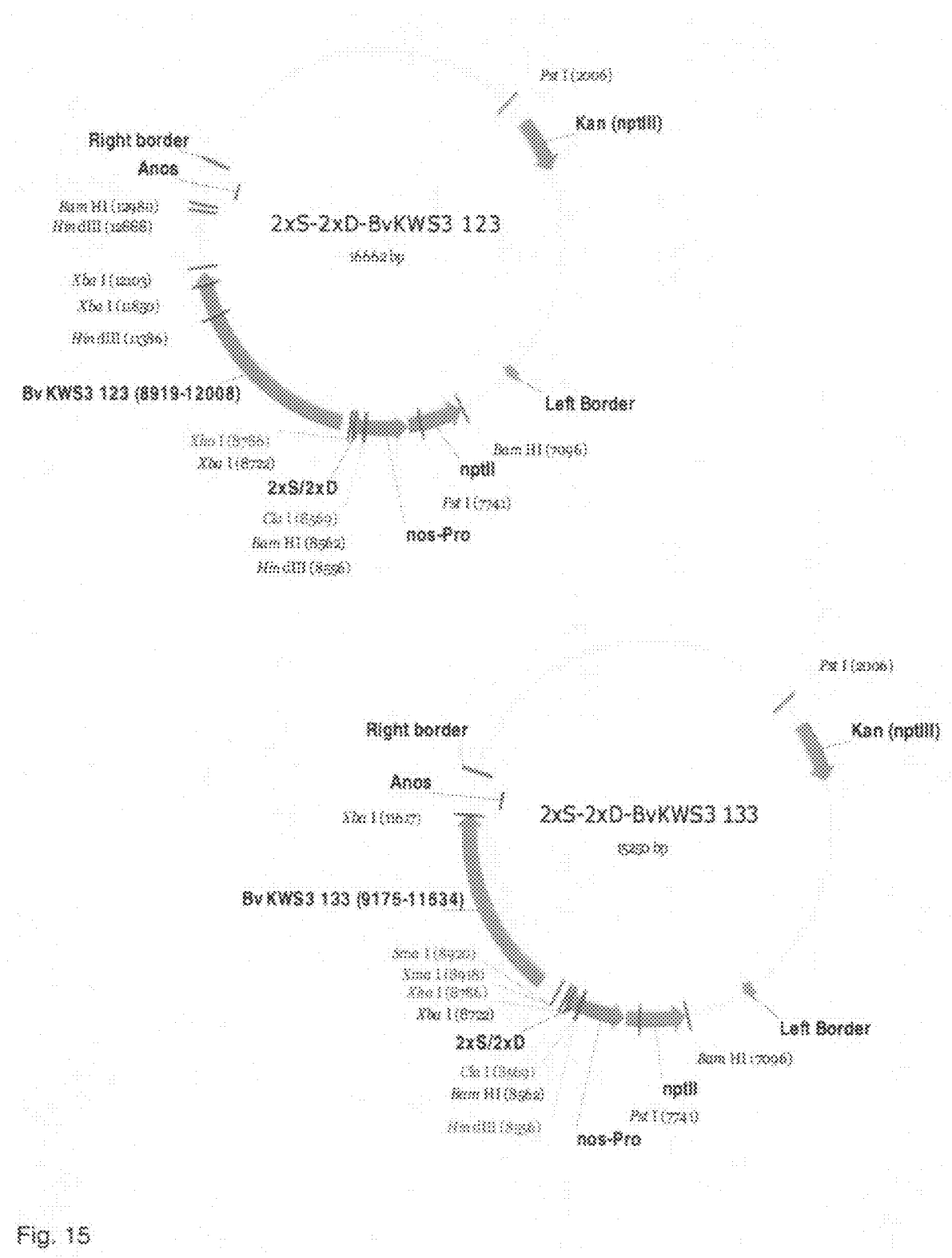
FIGS. 15 and 16 show combinations of full-length R-Gene 123, 133, 135, 165 with the synthetic promoter 2xS-2xD.
Figure 16:
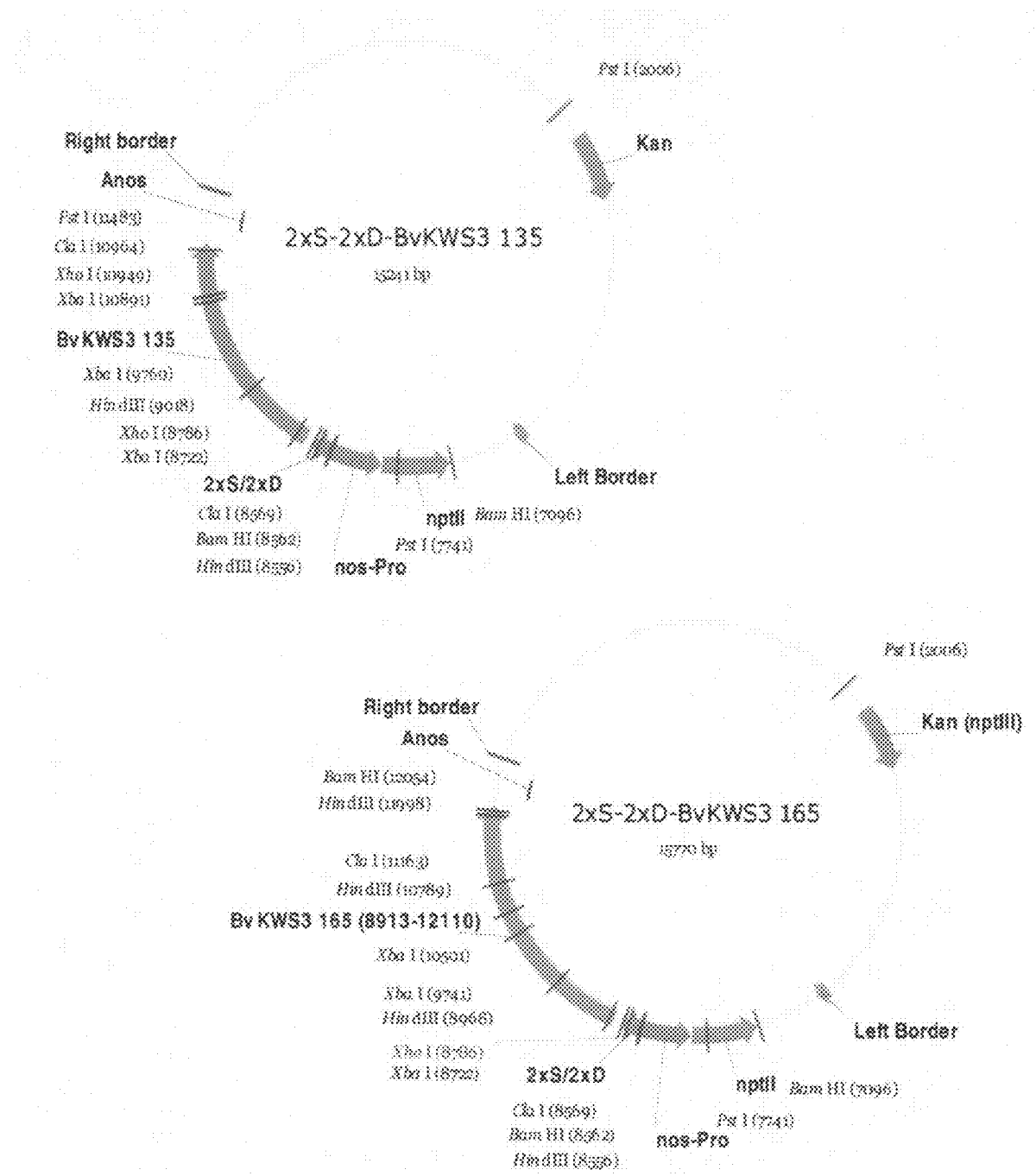
Figure 17:
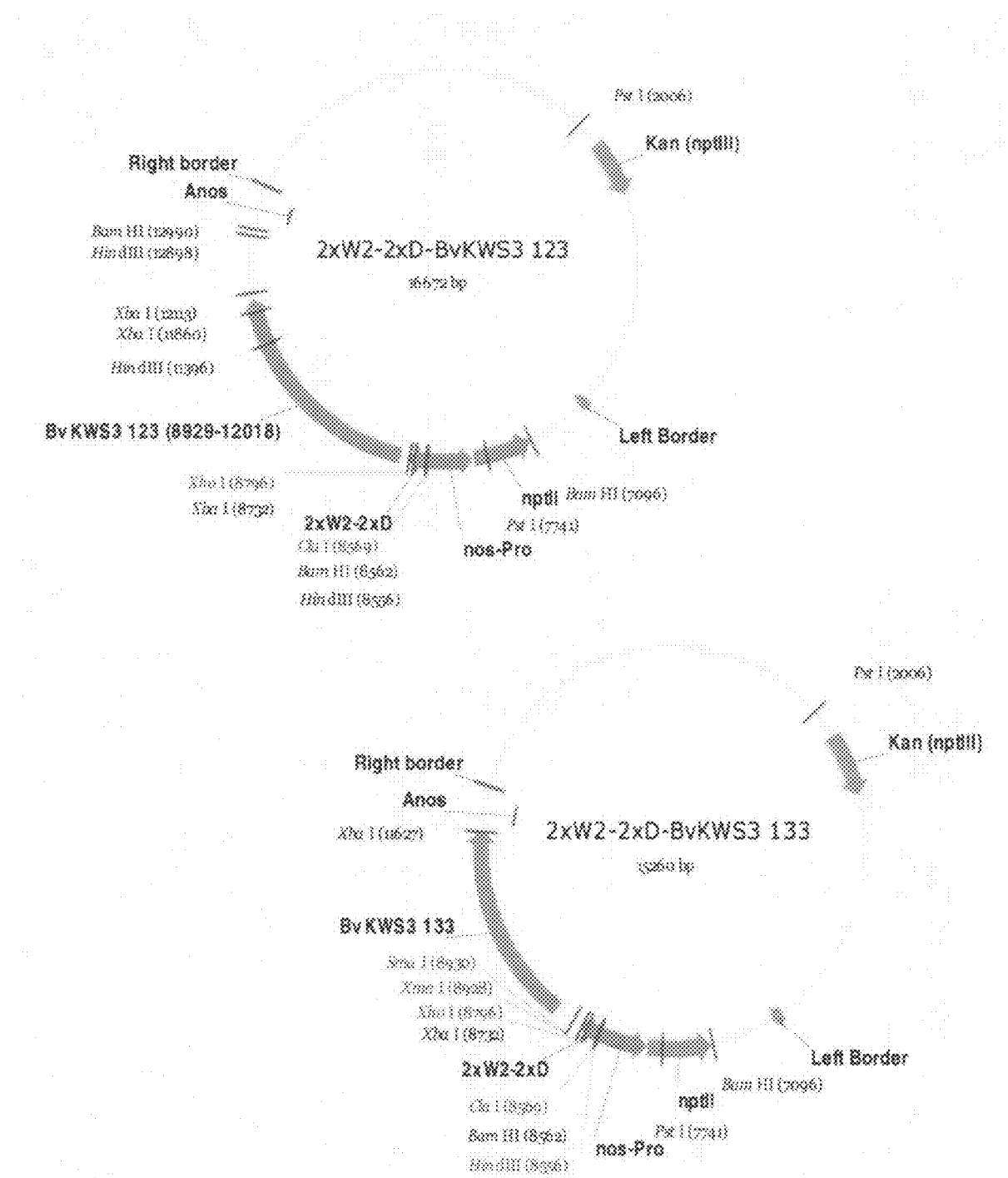
FIGS. 17 and 18 show combinations of full-length R-gene 123, 133, 135, 165 with the synthetic promoter $2xW_2$-2xD.
Figure 18:
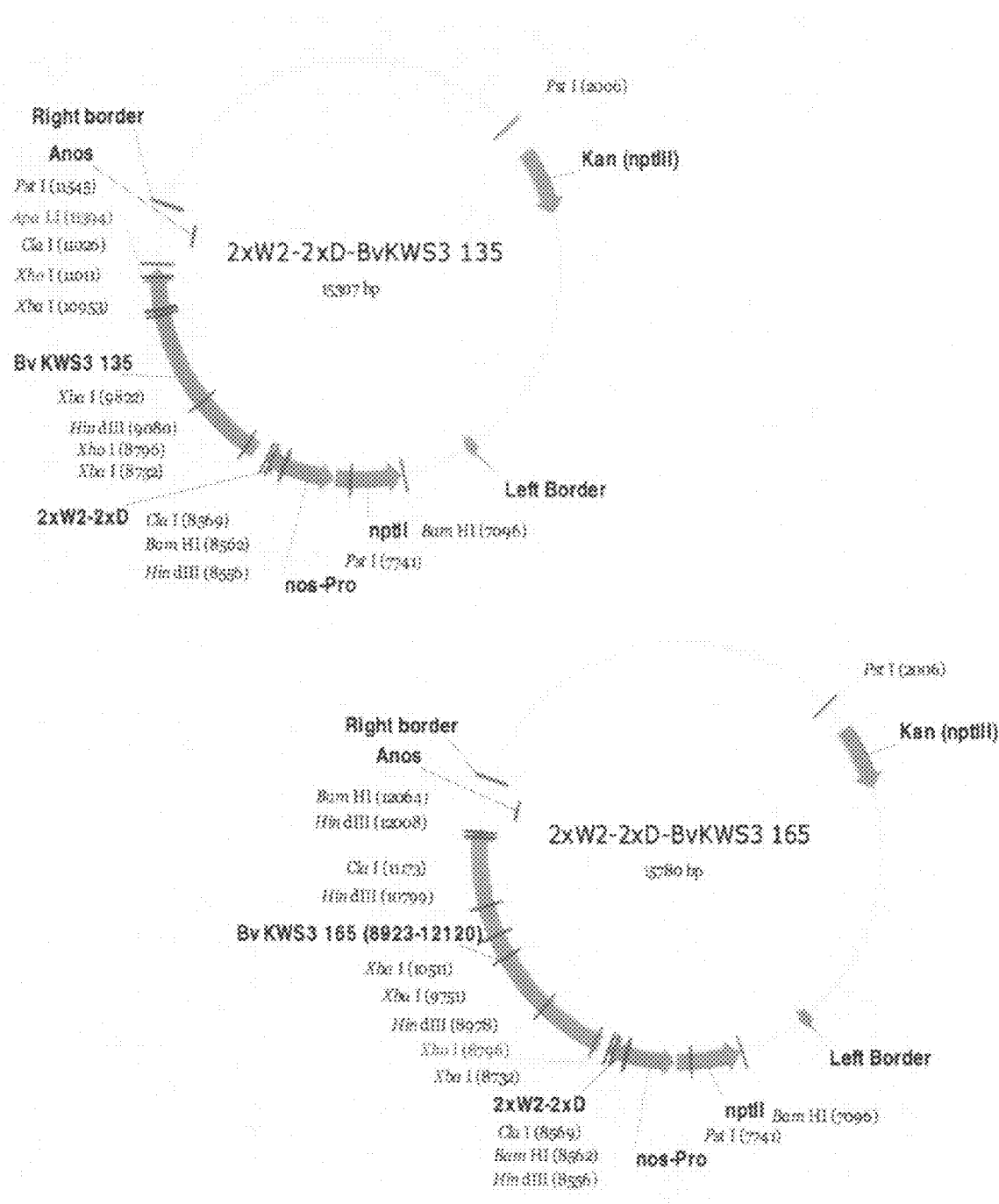

The comparison of the 2xS-2xD promoter characteristics with the variants 2xS-4xD, 4xS-2xD and 4xS-4xD showed that the average promoter strength was increased by the use of tetramers in comparison to the promoters constructed of dimers (FIG. 14). In addition, the pathogen inducibility of dimer-dimer promoter (2xS-2xD) climbed above the tetramer-dimer and dimer-tetramer promoters (4xS-2xD, 4xS-2xD) to the tetramer-tetramer promoter (4xS-4xD) at all measurement intervals (Table 1).

TABLE 1

Pathogen inducibility of the promoters 2xS-2xD, 4xS-2xD, 2xS-4xD und 4xS-4xD in transgenic sugar beets following infection with *Cercospora beticola*.

| Promotor (number of independent transformants) | 1. Day | 2. Day | 3. Day | 4. Day |
|---|---|---|---|---|
| 2xS-2xD (13 lines) | 1.9 | 3.6 | 27 | 59 |
| 4xS-2xD (14 lines) | 3.1 | 4.8 | 52 | 135 |
| 2xS-4xD (15 lines) | 1.4 | 9.2 | 54 | 87 |
| 4xS-4xD (15 lines) | 2.9 | 9.8 | 90 | 93 |

Shown is the average value of the pathogen induction of 13-15 independent transformants (lines) per promoter construct 1-4 days following inoculation.

Parallel with the increase in the promoter strength and the pathogen inducibility there results an increase in the base activity of the promoters which contain the tetramers (Table 2).

TABLE 2

Base activity of promoters 2xS-2xD, 4xS-2xD, 2xS-4xD und 4xS-4xD in leaves of transgenic sugar beets.

| Promotor (number of independent transformants) | 1. Day | 2. Day | 3. Day | 4. Day |
|---|---|---|---|---|
| 2xS-2xD (13 lines) | 4.7 | 5.5 | 5.2 | 2.6 |
| 4xS-2xD (14 lines) | 14.2 | 21 | 7.8 | 11 |
| 2xS-4xD (15 lines) | 24.6 | 13.3 | 7 | 22.3 |
| 4xS-4xD (15 lines) | 35.5 | 20.3 | 6.3 | 20 |

Shown is the average value of the base activity of 13-15 independent transformants (lines) per promoter construct, which were measured in the 4 day infection experiment as non-infected controls. The base activity provides the behavior or relationship of the reporter gene activity of the transgenic plants in comparison to the non-specific background activity of non transgenic plants.

This example shows that the promoter characteristics important to the concept, such as promoter strength, pathogen inducibility and base activity, can be regulated by the number of the cis-elements and that optimal promoter variants can be created for the respective technical conversion. The optimal number of cis-elements of pathogen inducible promoters is, in the experimental example, with regard to the pathogen inducibility, greater than the dimer solution described by Rushton et al., 2002.

Producing Fungus Resistant by Transformation of the Pathogen Inducible Resistance Gene.

For increasing the fungal resistance of sugar beets the promoters 2xS-2xD or, as the case may be, $2xW_2$-2xD were respectively combined with the four R-genes BvKWS3_123, BvKWS3_133, BvKWS3_135 and BvKWS3_165 and transformed in sugar beets. Then the 13,959 or, as the case may be, 13,969 kb sized binary vectors 2xS-2xD-luc-kan and 2xW2-2xD-luc-kan were cleaved with Sac1 and the cleaved locations were filled by T4-DNA polymerase treatment. Subsequently the vectors were re-sectioned with XhoI, electrophoretically separated and the 12,284 or, as the case may be, 12,294 kb size vectors were separated from the 1,675 kb size luciferase gene and isolated.

The isolation of the ZR resistance gene occurred from the vectors p70S-BvKWS3_123, p70S-BvKWS3_133, p70S-BvKWS3_135 and p70S-BvKWS3_165. For this, the vectors were first linearized with Not1 and the cleavage points were filled by Klenow treatment. The vectors were then cut with XhoI and the R-gene isolated. The resulting vectors were given the designations 2xS-2xD-BvKWS3_123, 2xS-2xD-BvKWS3_133, 2xS-2xD-BvKWS3_135 und 2xS-2xD-BvKWS3_165 or, as the case may be, $2xW_2$-2xD-BvKWS3_123, $2xW_2$-2xD-BvKWS3_133, $2xW_2$-2xD-BvKWS3_135 and $2xW_2$-2xD-BvKWS3_165 (FIG. 15-18). The binary vectors were used as described for the production of transgenic sugar beets.

Identification of Fungal Resistant Sugar Beets by Resistance Testing with Plant Pathogenic Fungi *Cercospora beticola*.

The elevated fungal resistance of the plants was observed in a fungal resistance test which is described in the following for exemplary purposes for the resistance testing for the sugar beet with respect to *Cercospora beticola*.

For the infection of sugar beets with the leaf spot inducer *C. beticola*, use was made of, besides the transgenic plants, sugar beets of the genotype 3DC4156 used for the transformation, in a greenhouse. Two weeks prior to the plant inoculation vegetable juice plates (40% Albani-vegetable juice) were spiked with the aggressive *C. beticola* isolate Ahlburg and incubated at 25° C. Directly prior to inoculation the agar with growing fungi is scratched off with the aid of an object carrier and some water. The concentration of mycellular fragments and fungal spores is determined using a counting cell chamber. The inoculum density is adjusted by dilution with water to a concentration of 20,000 fragments/ml. For infection the 10-12 week old plants were dipped inverted in a 5 L glass beaker filled with the inoculum. Per line to be examined, 30 plants were inoculated and the plants were set up randomized in the greenhouse.

The plants were incubated following inoculation for 4 days at 28° C. and 95% humidity in a greenhouse. After the fourth day the humidity was reduced to 60-70%. Two, three and four weeks following inoculation the leaf drop is optically evaluated using the Kleinwanzlebener Saatzucht (KWS) rating scheme (1970) (1=healthy leaves, 9=100% destroyed leaves). Transgenic lines, which were transformed with the constructs 2xS-2xD-BvKWS3_123, 2xS-2xD-BvKWS3_133, 2xS-2xD-BvKWS3_165, $2xW_2$-2xD-BvKWS3_123, $2xW_2$-2xD-BvKWS3_133, $2xW_2$-2xD-BvKWS3_135 or $2xW_2$-2xD-BvKWS3_165, showed, in comparison the control, an elevated fungal resistance (Table 3).

TABLE 3

Elevated resistance of transgenic sugar beets against the plant pathogenic fungus *Cercospora beticola*.

| Contol (not transgenic) | | Transgenic Line line- | | | |
|---|---|---|---|---|---|
| T3[1] | AUDPC[2] | designation | T3[1] | AUDPC[2] | Construct |
| 6.0 | 220 | PR68-6  | 4.6 | 169 | 2xS-2xD-BvKWS3-133 |
| 6.8 | 193 | PR74-73 | 6.1 | 157 | 2xS-2xD-BvKWS3-123 |
| 4.1 | 167 | PR75-8  | 2.8 | 132 | 2xS-2xD-BvKWS3-165 |
| 6.0 | 220 | PR69-15 | 5.3 | 177 | 2xW$_2$-2xD-BvKWS3-133 |
| 7.0 | 226 | PR70-32 | 5.5 | 182 | 2xW$_2$-2xD-BvKWS3-123 |
| 6.8 | 193 | PR77-42 | 5.6 | 155 | 2xW$_2$-2xD-BvKWS3-135 |
| 6.8 | 229 | PR71-41 | 5.6 | 182 | 2xW$_2$-2xD-BvKWS3-165 |

[1]Third and last rating value of the resistance test (1 = healthy, 9 = 100% damaged leaf surface).
[2]AUDPC (area under disease progress curve) value determined over 3 rating periods (T1-T3). The AUDPC encompasses the progression of the strength of infestation of multiple rating time points into a single value.

Figure 19:
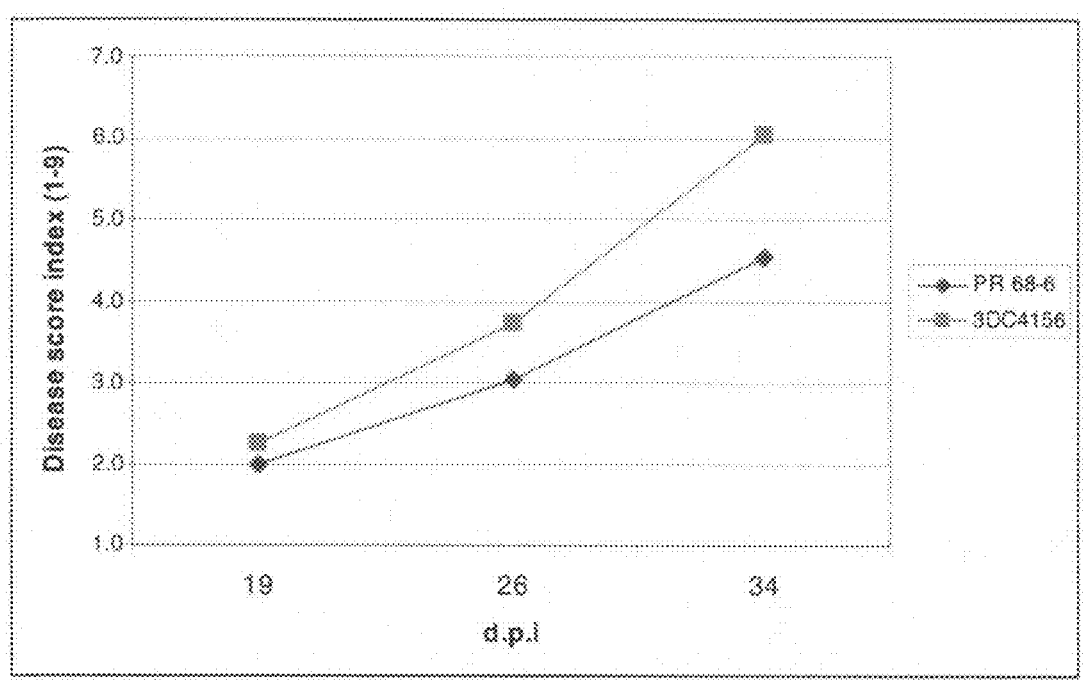
FIG. 19 shows the elevated resistance of the transgenic sugar beet line PR68-6 against injurious fungus *Cercospora beticola* in comparison to the non-transgenic control 3DC4156.
Figure 20:
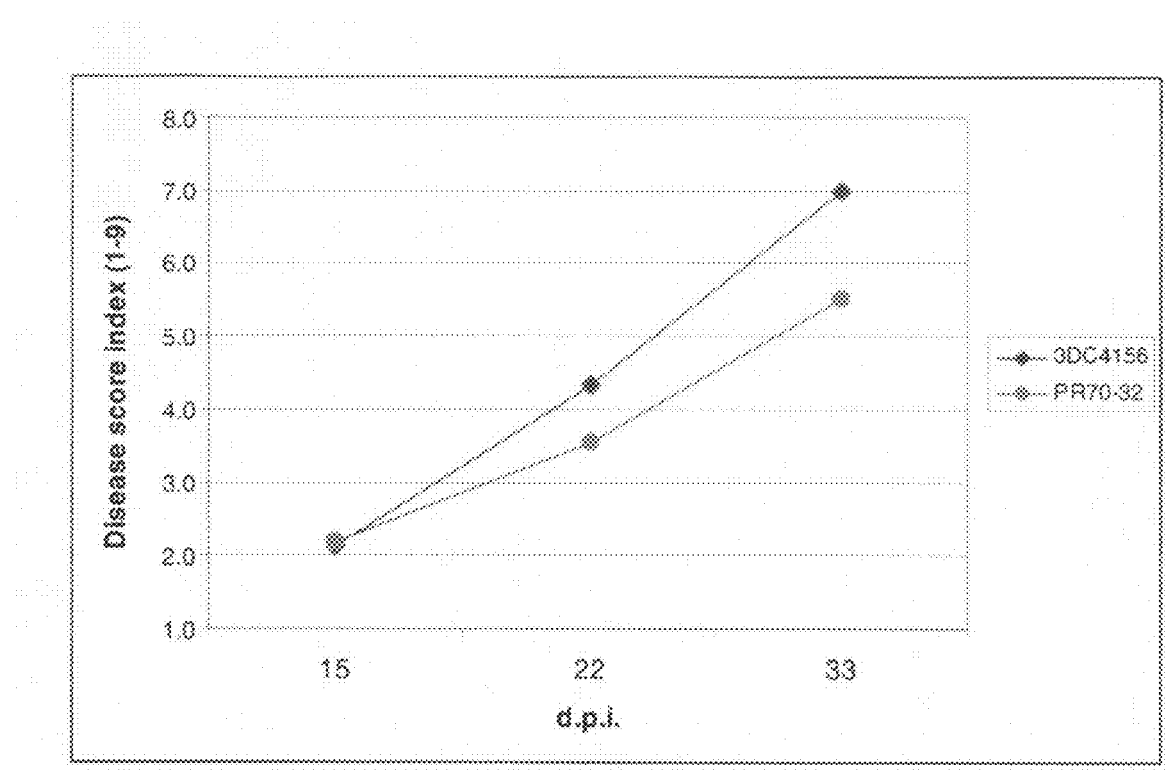
FIG. 20 shows the elevated resistance of the transgenic sugar beet line PR70-32 against *Cercospora beticola* in comparison to the non-transgenic control 3DC4156.

The analysis of the time progression of the infestation development in the transformants PR68-6 and PR70-32 over the three rating periods shows that with advance of experiment duration the difference in the infestation development between control and transgenic lines increases (FIGS. 19 and 20). These results show that the induced expression of different R-genes of the sugar beet leads, with the aid of the pathogen specific promoter, to an elevated fungal resistance.

Producing Fungal Resistant Plants by Transformation of the N-Terminal Area of the R-Gene Under the Control of Pathogen Responsive Promoters.

In order to produce fungal resistant plants with use of the N-terminal section of the R-gene, the condensed or shortened R-genes 13033_#159, 135_#147, 165_#175 and Bv12069 were combined with the promoters 2xS-2xD and 2xW2-2xD and transformed in sugar beets.

For this, the 13,959 or, as the case may be, 13,969 kb sized binary vectors 2xS-2xD-luc-kan and 2xW2-2xD-luc-kan were cleaved with SacI and the cleavage points were filled by treatment with T4-DNA polymerase. Subsequently, the vectors were further cut with XhoI, gel-electrophoretically separated, and the 12,284 or, as the case may be, 12,294 kb size vectors were separated from the 1,675 size luciferase gene and isolated.

Figure 21:
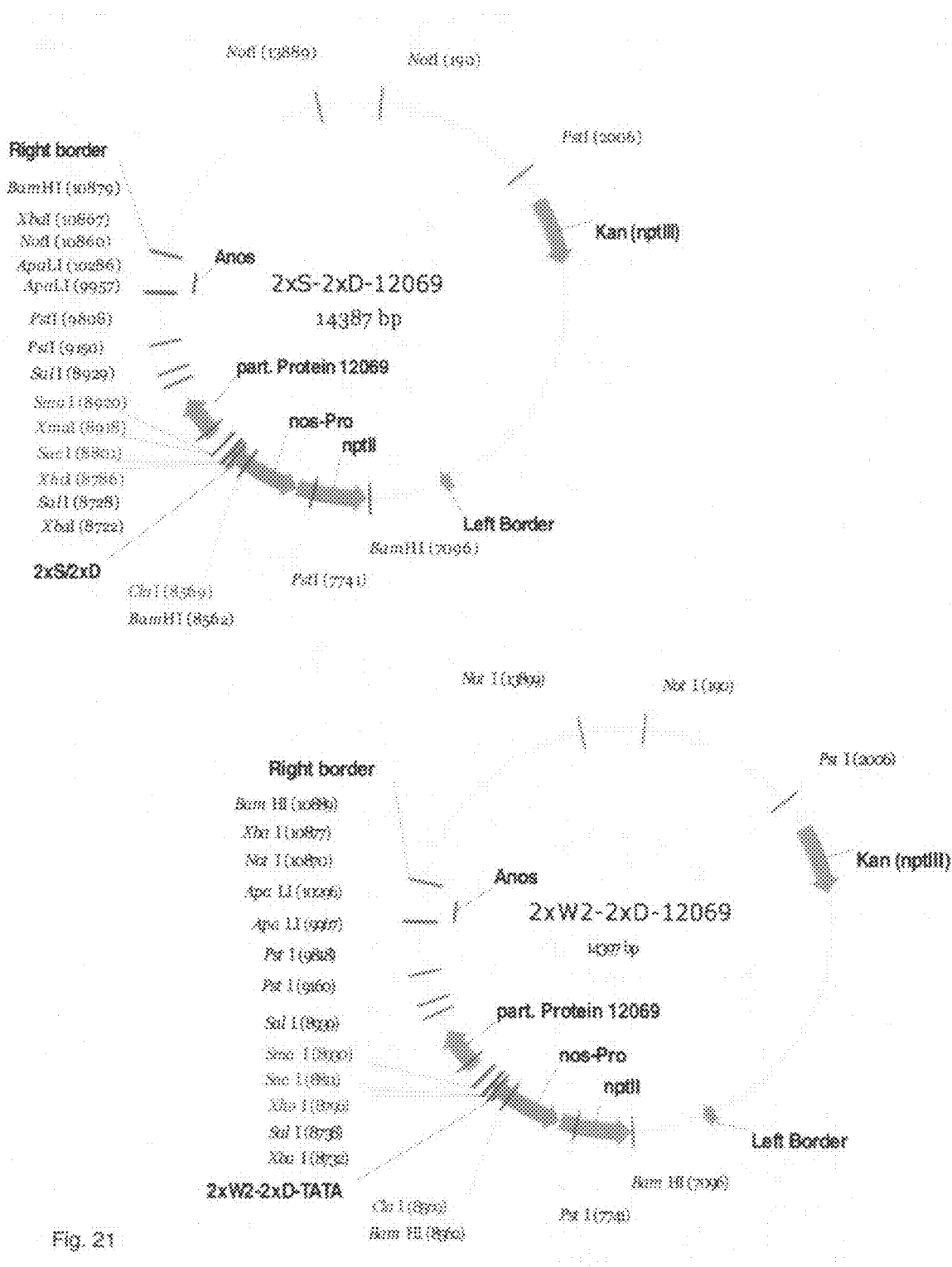
FIGS. 21 and 22 show the combination of the N-terminal areas of the R-gene, 165_#176 and 12069 with the synthetic promoters 2xS-2xD and $2xW_2$-2xD.
Figure 22:
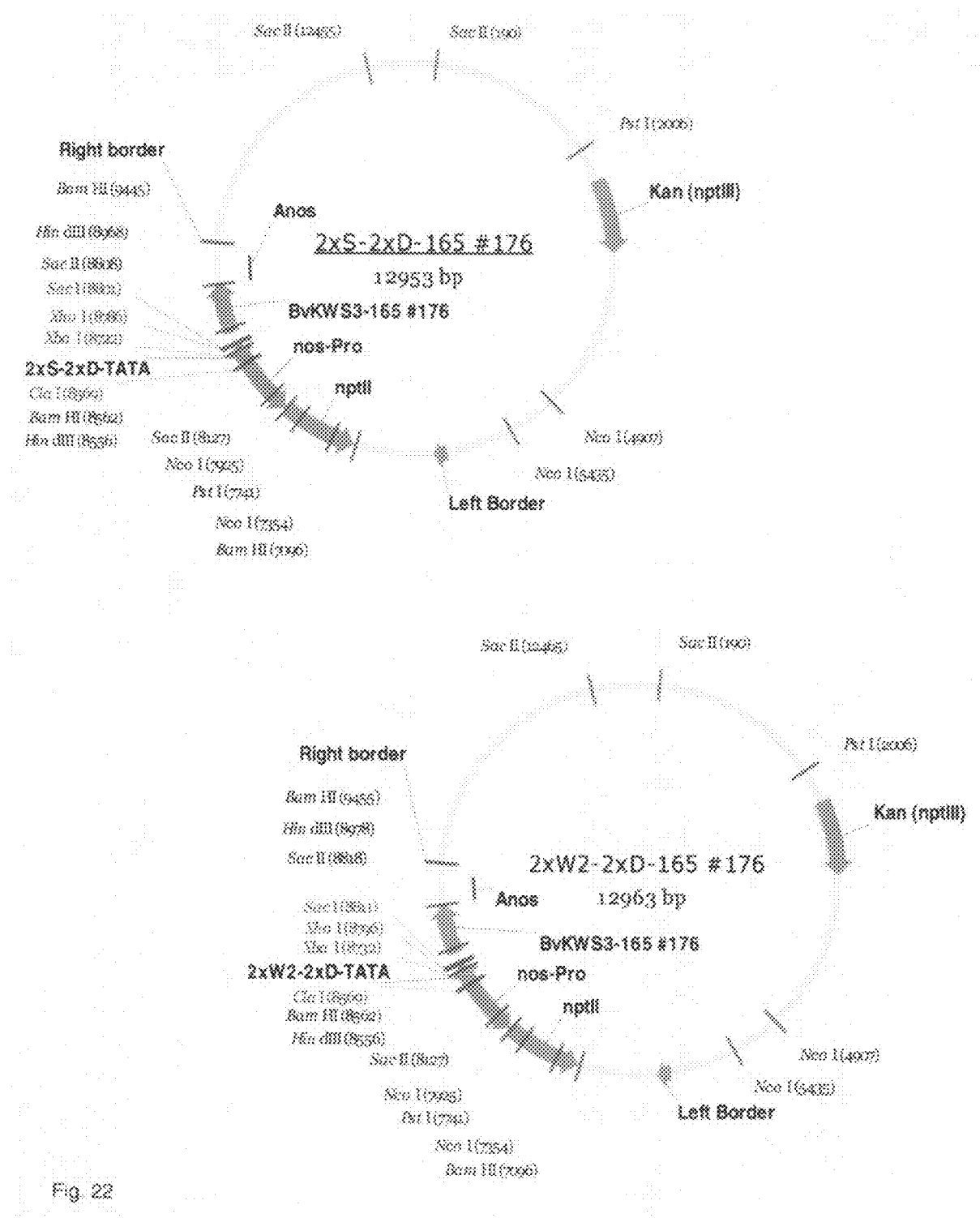

The isolation of the shortened R-gene occurred from the vectors p70S-12069, p70S-13033_#159, p70S-135_#147 and p70S-165_#175. The vectors were first linearized with XbaI, the DNA ends were filled by Klenow treatment, and the vectors were further cut with XhoI. The isolated R-gene fragments were then cloned in the prepared binary vectors. The resulting vectors were given the designations 2xS-2xD-12069, 2xS-2xD-13033_#159, 2xS-2xD-135_#147, 2xS-2xD-165_#175 or, as the case may be, 2xW2-2xD-12069, 2xW2-2xD-13033_#159, 2xW2-2xD-135_#147, 2xW2-2xD-165_#175 (FIG. 21-22). The binary vectors were transformed as described in sugar beets and the fungal resistant plants were identified by a *Cercospora beticola* resistance test.

REFERENCES

Altschul, S. F. et al. (1990). Basic Local Alignment search tool, J. Mol. Biol. 215: 403-410

An, G. (1987). Binary Ti vectors for plant transformation and promoter analysis. Methods Enzymol. 153, 292-305.

Bairoch et al., (1996) The PROSITE database, its status in 1995. *Nucleic Acids Res* 24:189-96

Ballavora A., Ercolana M R., Weiss J., Meksem K., Bormann C. A. 1, Oberhagemann P., Salamini F., Gebhardt C. (2002). The R1 gene for potato resistance to late blight (Phytophthora infestans) belongs to the leucine zipper/NBS/LRR class of plant resistance genes. Plant J. 30(3): 361-71.

Bendahmane A., Farnham G., Moffett P., and Baulcombe D. C. (2002). Constitutive gain-of-function mutants in a nucleotide binding site-leucine rich repeat protein encoded at the Rx locus of potato. Plant J. October; 32(2):195-204.

Frost D., Way H., Howles P., Luck J., Manners J., Hardham A., Finnegan J., and Ellis J. (2004). Tobacco transgenic for the flax rust resistance gene L expresses allele-specific activation of defence responses. Mol Plant Microbe Interact. 17(2):224-32.

Hennig, J., Dewey, R. E., Cutt, J. R, and Messig, D. F. (1993). Pathogen, salicylic acid and developmental dependent expression of a beta-1,3-glucanase/GUS gene fusion in transgenic tobacco plants. Plant J. 4(3):481-93.

Howles P., Lawrence G., Finnegan J., McFadden H., Ayliffe M., Dodds D., and Ellis J. (2005). Autoactive Alleles of the Flax L6 Rust Resistance Gene Induce Non-Race-Specific Rust Resistance Associated with the Hypersensitive Response. Mol Plant Microbe Interact. 18(6):570-582.

Huang S., an der Vossen E. A., Kuang H., Vlesshouwers V. G., Zhang N., Borm, T. J., van Eck H. J., Baker B., Jacobsen E., and Visser R. G. (2005). Comparative genomics enabled the isolation of the R3a late blight resistance gene in potato. Plant J. 42(2):251-61.

Lindsey, K., Gallois, P., and Eady, C. (1991). Regeneration and transformation of sugar beet by *Agrobacterium tumefaciens*. Plant Tissue Culture Manual B7: 1-13; Kluwer Academic Publishers.

Lupas, A., Van Dyke M., and Stock J. (1991) Predicting coiled coils from protein sequences. *Science* 252:1162-4.

Martin, G. B., Bogdanove, A. J., and Sessa, G. (2003). Understanding the functions of plant disease resistance proteins. Annu. Rev. Plant Biol. 54: 23-61.

Martini, N., Egen, M., Rüntz, I., and Strittmatter, G. (1993). Promoter sequences of a potato pathogenesis-related gene mediate transcriptional activation selectively upon fungal infection. Mol Gen Genet 236: 179-186.

Oldroyd, G. E. D., and Staskawicz, B. J. (1998). Genetically engineered broad-spectrum disease resistance in tomato. Proc Natl Acad Sci USA. 95(17): 10300-10305

Rushton P. J., Reinstadler A., Lipka V., Lippok B., Somssich I. E. (2002). Synthetic plant promoters containing defined regulatory elements provide novel insights into pathogen- and wound-induced signalling. Plant Cell 14(4):749-62.

Samac, D. A. and Shah, D. M. (1991). Developmental and Pathogen-Induced Activation of the *Arabidopsis* Acidic Chitinase Promoter. Plant Cell. 3(10):1063-1072.

Schmidt K., Heberle B., Kurrasch J., Nehls R., and Stahl D. J. (2004). Suppression of phenylalanine ammonia lyase expression in sugar beet by the fungal pathogen *Cercospora beticola* is mediated at the core promoter of the gene. Plant Mol. Biol., 55: 835-852.

Sonnhammer, E. L., Eddy, S. R., and Durbin, R. D. (1997) Pfam: A comprehensive database of protein domain families based on seed alignments. Proteins 28:405-20.

Tang X., Xie M., Kim Y. J., Zhou J., Klessig D. F., Martin G. B. (1999). Overexpression of Pto activates defence responses and confers broad resistance. Plant Cell 11 (1): 15-29.

Tian Y., Fan L., Thurau T., Jung C., and Cai D. (2004). The absence of TIR-type resistance gene analogues in the sugar beet (*Beta vulgaris* L.) genome. J. Mol. Evol. 58(1):40-53.

Traut, T. W. (1994). The functions and consensus motifs of nine types of peptide segments that form different types of nucleotide binding sites. Eur. J. Biochem. 222:9-19.

The invention claimed is:

1. An isolated nucleic acid, which codes for an autoactivated resistance protein for producing a resistance against pathogens in plants, wherein the nucleic acid consists of a limited part of an NBS-LRR-resistance gene, which extends from the 5' end of the coding region of the NBS-LRR-resistance gene downstream to the beginning to the NBS-domain of the NBS-LRR-resistance gene, wherein the NBS-LRR resistance gene is not a TIR-NBS-LRR resistance gene, and wherein the autoactivated resistance protein excludes a P-loop.

2. The isolated nucleic acid according to claim 1, wherein the nucleic acid codes for an amino acid sequence with the sequence motif DAE.

3. The isolated nucleic acid according to claim 1, wherein the nucleic acid codes for an amino acid sequence with the sequence motif AVLXDAE, said sequence motif identified as SEQ ID NO: 21.

4. The isolated nucleic acid according to claim 1, with a nucleotide sequence selected from the group consisting of:
 a) the nucleotide sequence according to SEQ ID NO: 1, or a nucleotide sequence fully complementary to the nucleotide sequence according to SEQ ID NO: 1;
 b) the nucleotide sequence according to SEQ ID NO: 2, or a nucleotide sequence fully complementary to the nucleotide sequence according to SEQ ID NO: 2;
 c) the nucleotide sequence according to SEQ ID NO: 3, or a nucleotide sequence fully complementary to the nucleotide sequence according to SEQ ID NO: 3;
 d) the nucleotide sequence according to SEQ ID NO: 4, or a nucleotide sequence fully complementary to the nucleotide sequence according to SEQ ID NO: 4;
 e) the nucleotide sequence according to SEQ ID NO: 16, or a nucleotide sequence fully complementary to the nucleotide sequence according to SEQ ID NO: 16; and
 f) a nucleotide sequence that hybridizes to any of the SEQ ID NO: 1, SEQ ID NO: 2, SEQ ID NO: 3, SEQ ID NO: 4, or SEQ ID NO: 16, or a nucleotide sequence that hybridizes to a sequence fully complementary to any of the SEQ ID NO: 1, SEQ ID NO: 2, SEQ ID NO: 3, SEQ ID NO: 4, or SEQ ID NO: 16, under high stringency conditions comprising hybridizing in 4×SSC at 65° C. and subsequent multiple washing in 0.1×SSC at 65° C. for a total of approximately 1 hour;
 wherein the nucleotide sequence encodes an autoactivated resistance protein.

5. The isolated nucleic acid according to claim 1, wherein the nucleotide sequence is from a NBS-LRR-resistance gene from sugar beet or potato.

6. The isolated nucleic acid according to claim 1, wherein the nucleotide sequence encodes a protein comprising an amino acid sequence selected from the group consisting of:
 a) SEQ ID NO: 13;
 b) SEQ ID NO: 14; and
 c) SEQ ID NO: 15.

7. A nucleic acid construct comprising
 a pathogen inducible promoter operably linked to the
 a nucleic acid according to claim 1.

8. The nucleic acid construct according to claim 7, wherein the pathogen inducible promoter is a synthetic promoter.

9. The nucleic acid construct according to claim 8, wherein the synthetic promoter includes one or more cis-element combinations selected from the group consisting of:
 a) a nxS-mxD-box;
 b) a nxW2-mxD-box; and
 c) a nxGst1-mxD-box;
 wherein n and m mean a natural number from 1 . . . 10.

10. The nucleic acid construct according to claim 9, wherein the cis-element combination includes:
 a) a nucleotide sequence of SEQ ID NO: 10;
 b) a nucleotide sequence of SEQ ID NO: 11;
 c) a nucleotide sequence of SEQ ID NO: 12; or
 d) a derivative of a nucleic acid sequence according to a) through c) with comparable characteristics.

11. A transgenic plant, transformed with the nucleic acid construct according to claim 1.

12. A transformed part of the transgenic plant according to claim 11.

13. Transformed seed of the transgenic plant according to claim 11.

14. A process for producing a transgenic plant or transgenic thereof with an increased resistance against pathogens, the process comprising transforming a plant or seed thereof with a nucleic acid, wherein the nucleic acid, which codes for an autoactivated resistance protein, consists of comprises a limited part of an NBS-LRR-resistance gene, which extends from the 5' end of the coding region of the NBS-LRR-resistance gene downstream to the beginning of the NBS-domain of the NBS-LRR-resistance gene, wherein the NBS-LRR-resistance gene is not a TIR-NBS-LRR-resistance gene, and wherein the autoactivated resistance protein excludes a P-loop.

15. The process according to claim 14, wherein the nucleic acid codes for an amino acid sequence with the sequence motif DAE.

16. The process according to claim 14, wherein the nucleic acid codes for an amino acid sequence with the sequence motif AVLXDAE.

17. The process according to claim 14, wherein the nucleic acid comprises a nucleotide sequence selected from the group consisting of:
 a) the nucleotide sequence according to SEQ ID NO: 1, or a nucleotide sequence fully complementary to the nucleotide sequence according to SEQ ID NO: 1;
 b) the nucleotide sequence according to SEQ ID NO: 2, or a nucleotide sequence fully complementary to the nucleotide sequence according to SEQ ID NO: 2;
 c) the nucleotide sequence according to SEQ ID NO: 3, or a nucleotide sequence fully complementary to the nucleotide sequence according to SEQ ID NO: 3;
 d) the nucleotide sequence according to SEQ ID NO: 4, or a nucleotide sequence fully complementary to the nucleotide sequence according to SEQ ID NO: 4;
 e) the nucleotide sequence according to SEQ ID NO: 16, or a nucleotide sequence fully complementary to the nucleotide sequence according to SEQ ID NO: 16; and
 f) a nucleotide sequence that hybridizes to any of the SEQ ID NO: 1, SEQ ID NO: 2, SEQ ID NO: 3, SEQ ID NO: 4, or SEQ ID NO: 16, or a nucleotide sequence that hybridizes to a sequence fully complementary to any of the SEQ ID NO: 1, SEQ ID NO: 2, SEQ ID NO: 3, SEQ ID NO: 4, or SEQ ID NO: 16, under high stringency conditions comprising hybridizing in 4×SSC at 65° C. and subsequent multiple washing in 0.1×SSC at 65° C. for a total of approximately 1 hour;
 wherein the nucleotide sequence encodes an autoactivated resistance protein.

18. The process according to claim 14, wherein the nucleotide sequence is from a NBS-LRR-resistance gene from sugar beet or potato.

19. The process according to claim 14, wherein the nucleic acid encodes a protein comprising an amino acid sequence selected from the group consisting of:
 a) SEQ ID NO: 13;
 b) SEQ ID NO: 14; and
 c) SEQ ID NO: 15.

20. The process according to claim 14, wherein the nucleotide sequence is operably linked to
 a pathogen inducible promoter.

21. The process according to claim 20, wherein the pathogen inducible promoter is a synthetic promoter.

22. The process according to claim 21, wherein the synthetic promoter includes one or cis-element combinations selected from the group consisting of:
 a) a nxS-mxD-Box;
 b) a nxW2-mxD-Box; and
 c) a nxGst1-mxD-Box;
wherein n and m mean a natural number from 1 . . . 10.

23. The process according to claim 22, wherein the cis-element combination includes:
 a) SEQ ID NO: 10;
 b) SEQ ID NO: 11; or
 c) SEQ ID NO: 12.

24. An isolated nucleic acid comprising a nucleotide sequence selected from the group consisting of:
 a) the nucleotide sequence according to SEQ ID NO: 1, or a nucleotide sequence fully complementary to the nucleotide sequence according to SEQ ID NO:1;
 b) the nucleotide sequence according to SEQ ID NO: 2, or a nucleotide sequence fully complementary to the nucleotide sequence according to SEQ ID NO: 2;
 c) the nucleotide sequence according to SEQ ID NO: 3, or a nucleotide sequence fully complementary to the nucleotide sequence according to SEQ ID NO: 3;
 d) the nucleotide sequence according to SEQ ID NO: 4, or a nucleotide sequence fully complementary to the nucleotide sequence according to SEQ ID NO: 4; and
 e) a nucleotide sequence that hybridizes to any of the SEQ ID NO: 1, SEQ ID NO: 2, SEQ ID NO: 3, or SEQ ID NO: 4 under high stringency conditions comprising hybridizing in 4×SSC at 65° C. and subsequent multiple washing in 0.1×SSC at 65° C. for a total of approximately 1 hour;
wherein the nucleotide sequence encodes an autoactivated resistance protein.

* * * * *